US008473045B2

(12) United States Patent
Terada et al.

(10) Patent No.: US 8,473,045 B2
(45) Date of Patent: Jun. 25, 2013

(54) METHOD FOR CONTROLLING DEVICE BY USING BRAIN WAVE AND BRAIN WAVE INTERFACE SYSTEM

(75) Inventors: Yoshihisa Terada, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 443 days.

(21) Appl. No.: 12/716,425

(22) Filed: Mar. 3, 2010

(65) Prior Publication Data

US 2010/0191140 A1 Jul. 29, 2010

Related U.S. Application Data

(63) Continuation of application No. PCT/JP2009/002968, filed on Jun. 26, 2009.

(30) Foreign Application Priority Data

Jul. 11, 2008 (JP) ................................ 2008-181645

(51) Int. Cl.
A61B 5/04 (2006.01)

(52) U.S. Cl.
USPC .......................................... 600/545; 600/544

(58) Field of Classification Search
USPC .................................................. 600/544, 545
See application file for complete search history.

(56) References Cited

U.S. PATENT DOCUMENTS 4,579,125 A * 4/1986 Strobl et al. .................. 600/544
6,647,296 B2 * 11/2003 Fischell et al. .................. 607/45
7,945,865 B2 * 5/2011 Adachi et al. ................. 715/863
2004/0034645 A1 2/2004 Manabe et al.
2005/0017870 A1 * 1/2005 Allison et al. ........... 340/825.19
2005/0085741 A1 * 4/2005 Hoskonen et al. ............ 600/544
2006/0111644 A1 * 5/2006 Guttag et al. ................. 600/544

(Continued)

FOREIGN PATENT DOCUMENTS

JP 06-121775 5/1994
JP 07-064709 3/1995

(Continued)

OTHER PUBLICATIONS

International Search Report for corresponding application No. PCT/JP2009/002968 dated Jul. 28, 2009.

(Continued)

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

The control method for a device includes steps of: presenting a visual stimulation concerning a manipulation menu for a device; measuring event-related potentials after the visual stimulation is presented, where event-related potentials based on a timing of presenting the visual stimulation as a starting point are measured from a potential difference between each of electrodes and at least one reference electrode respectively worn on a face and in an ear periphery of a user; from each of the measured event-related potentials, extracting electroencephalogram data which is at 5 Hz or less and contains a predetermined time section, and combining the extracted electroencephalogram data into electroencephalogram characteristic data; comparing the electroencephalogram characteristic data against reference data prepared in advance for determining a desire to select an item in the manipulation menu; and, based on a comparison result, executing a manipulation of the device corresponding to the item.

16 Claims, 21 Drawing Sheets

U.S. PATENT DOCUMENTS

| | | | | |
|---|---|---|---|---|
| 2006/0258930 | A1 * | 11/2006 | Wu et al. | 600/383 |
| 2007/0208269 | A1 * | 9/2007 | Mumford et al. | 600/546 |
| 2007/0270706 | A1 * | 11/2007 | Merilainen et al. | 600/544 |
| 2007/0287930 | A1 * | 12/2007 | Sutton | 600/544 |
| 2008/0294033 | A1 | 11/2008 | Yamazaki | |

FOREIGN PATENT DOCUMENTS

| | | |
|---|---|---|
| JP | 09-038037 | 2/1997 |
| JP | 11-203022 | 7/1999 |
| JP | 2004-016658 | 1/2004 |
| JP | 2004-086768 | 3/2004 |
| JP | 2005-018167 | 1/2005 |
| JP | 2005-034620 | 2/2005 |
| WO | WO 2007066451 A1 * | 6/2007 |

OTHER PUBLICATIONS

Form PCT/ISA/237 and partial English translation.

* cited by examiner

FIG.3

| | | | MEASUREMENT ELECTRODE | | | | | | |
|---|---|---|---|---|---|---|---|---|---|
| | | AVERAGE | ABOVE LEFT EAR | ALONGSIDE LEFT EYE | ABOVE LEFT EYE | NOSE | ABOVE RIGHT EYE | ALONGSIDE RIGHT EYE | ABOVE RIGHT EAR |
| REFERENCE ELECTRODE | ABOVE LEFT EAR | **47.7%** | – | 48.4% | 56.6% | 43.8% | 53.4% | 36.9% | 46.9% |
| | ALONGSIDE LEFT EYE | **47.0%** | 48.4% | – | 57.2% | 40.9% | 45.6% | 37.8% | 51.9% |
| | ABOVE LEFT EYE | **54.1%** | 56.6% | 57.2% | – | 63.8% | 31.6% | 54.4% | 61.3% |
| | NOSE | **50.6%** | 43.8% | 40.9% | 63.8% | – | 55.6% | 40.6% | 58.8% |
| | ABOVE RIGHT EYE | **52.7%** | 53.4% | 45.6% | 31.6% | 55.6% | – | 65.9% | 63.8% |
| | ALONGSIDE RIGHT EYE | **47.9%** | 36.9% | 37.8% | 54.4% | 40.6% | 65.9% | – | 51.6% |
| | ABOVE RIGHT EAR | **55.7%** | 46.9% | 51.9% | 61.3% | 58.8% | 63.8% | 51.6% | – |

FIG.6

| | | | MEASUREMENT ELECTRODE | | | | | | |
|---|---|---|---|---|---|---|---|---|---|
| | | AVERAGE | ABOVE LEFT EAR | ALONGSIDE LEFT EYE | ABOVE LEFT EYE | NOSE | ABOVE RIGHT EYE | ALONGSIDE RIGHT EYE | ABOVE RIGHT EAR |
| REFERENCE ELECTRODE | LEFT MASTOID | **57.8%** | 50.0% | 62.5% | 67.5% | 59.1% | 62.8% | 48.4% | 54.4% |
| | RIGHT MASTOID | **66.6%** | 52.2% | 68.8% | 75.0% | 64.7% | 75.3% | 62.2% | 68.1% |

FIG. 17

| CORRECT-INCORRECT INDEX | SAMPLE POINT NUMBER | | | | | | |
|---|---|---|---|---|---|---|---|
| | 1 | 2 | 3 | | 34 | 35 | 36 |
| 1 | −8.02974 | 1.776736 | 10.91293 | ··· | 4.805759 | 8.087556 | 10.20504 |
| −1 | 11.1797 | 19.85782 | 27.47941 | ··· | 4.163331 | 2.573634 | 1.306148 |
| −1 | 5.431802 | 20.89254 | 31.81867 | ··· | −9.33677 | −14.4036 | −16.6116 |
| −1 | −25.2195 | −17.6982 | −0.56946 | ··· | 6.867737 | 8.708123 | 8.388034 |
| −1 | −1.74139 | −1.71906 | −2.7203 | ··· | −10.3803 | −10.3859 | −8.80758 |
| 1 | 11.8559 | 5.912404 | 4.894292 | ··· | 26.6639 | 19.7545 | 9.165509 |
| −1 | 10.15955 | 5.737885 | 1.741629 | ··· | −1.26159 | −7.27133 | −12.8301 |
| −1 | −20.2631 | −21.6689 | −12.5558 | ··· | 1.149007 | 1.223278 | 0.912728 |
| ⋮ | ⋮ | ⋮ | ⋮ | ⋮ | ⋮ | ⋮ | ⋮ |
| −1 | −12.8761 | −2.41456 | 9.181442 | ··· | 12.40866 | 17.72715 | 18.35198 |
| −1 | 5.670069 | −3.83451 | −9.76014 | ··· | −9.28154 | −14.6623 | −19.1203 |
| −1 | −6.8839 | −6.80169 | −4.54927 | ··· | 7.141707 | 7.07167 | 3.416733 |
| 1 | 10.00742 | 3.487835 | 0.975253 | ··· | 3.752458 | 9.888899 | 16.3149 |

| ELECTRODE POSITION | DISTINCTION RATIO |
|---|---|
| (1) ABOVE LEFT EYE BASED ON RIGHT MASTOID AS REFERENCE ELECTRODE | 75.0% |
| (2) ABOVE RIGHT EYE BASED ON RIGHT MASTOID AS REFERENCE ELECTRODE | 75.3% |
| (3) ABOVE RIGHT EAR BASED ON RIGHT MASTOID AS REFERENCE ELECTRODE | 68.1% |
| **PRESENT INVENTION** | **80.6%** |
| | |
| Pz | 81.3% |

| | (a)DISTINCTION RATIO WHEN NORMAL | (b)DISTINCTION RATIO WHEN FACIAL ELECTRODE (ABOVE RIGHT EAR) IS DETACHED | (c)DISTINCTION RATIO WHEN EAR ELECTRODE (RIGHT EAR) IS DETACHED |
|---|---|---|---|
| ON THE BASIS OF RIGHT EAR ONLY | 80.6% | 75.0% | 0.0% |
| PRESENT INVENTION (EMBODIMENT 2) | 80.6% | 75.6% | 69.1% |

METHOD FOR CONTROLLING DEVICE BY USING BRAIN WAVE AND BRAIN WAVE INTERFACE SYSTEM

This is a continuation of International Application No. PCT/JP2009/002968, with an international filing date of Jun. 26, 2009, which claims priority of Japanese Patent Application No. 2008-181645, filed on Jul. 11, 2008, the contents of which are hereby incorporated by reference.

BACKGROUND OF THE INVENTION

1. Field of the Invention

The present invention relates to a device manipulation interface technique of measuring an electroencephalogram of a user and, based on the measured electroencephalogram, enabling control of a device as desired by the user. More specifically, the present invention relates to a device manipulation interface technique for being incorporated in a wearable device such as a head-mount display (HMD) to make it possible to select and activate a function of the wearable device or another device on the basis of an electroencephalogram of a user.

2. Description of the Related Art

In recent years, wearable devices such as head-mount displays (HMD) are gaining prevalence due to decreases in the size and weight of devices. As interfaces of many devices, hardware-based methods are in use, e.g., pressing a button, moving a cursor to make a decision, and manipulating a mouse while looking at a screen. However, if the aforementioned physical manipulations are required when controlling a device whose main body has a small size and which is characterized to be handsfree, e.g., an HMD, the handsfree feature will be undermined, thus being ineffective. Therefore, attention is drawn to interfaces for controlling a device without performing any physical manipulations, specifically, easy-to-use interfaces utilizing an electroencephalogram that make it possible to control a device by merely thinking.

An electroencephalogram is an encephalic activity (electrical activity of cranial nerve cells) measured as an electrical signal based on a difference in potential between a reference electrode and an measurement electrode. An example of an interface utilizing an electroencephalogram is a method and apparatus of determining a human psychological state and the like by utilizing an event-related potential which is described in Japanese Laid-Open Patent Publication No. 2005-34620 (herein after "Patent Document 1").

Patent Document 1 discloses a technique of determining an option which a user wishes to select by utilizing a characteristic signal of an event-related potential of his or her electroencephalogram.

Specifically, an electroencephalogram interface is realized in which an electrode is worn on the parietal; words are randomly displayed on a screen; and a word which is selected by a user is determined by utilizing a positive component (P300 component) that appears in a time slot from 300 ms to 500 ms based on the timing of displaying the word which the user wishes to select as a starting point, for example.

In a conventional electroencephalogram measurement, electrodes are worn according to the position notation of the International 10-20 system, such that measurement is performed with a measurement electrode being worn on the parietal. In Patent Document 1, an electroencephalogram measurement is performed by using a characteristic signal at a Pz (median parietal) position or a Cz (median center) position according to the International 10-20 system. It is known that the characteristic signal utilized in Patent Document 1 is intensely measured at the location of the Pz position. Therefore, Pz is mainly used as an electrode position of conventional electroencephalogram interfaces.

The inventors have actually constructed an interface which determines an item that is selected by a user from among four options that are displayed on a TV screen by utilizing an electroencephalogram which is measured at the Pz position. In the following, any mention of an "electroencephalogram interface being constructed" will mean a similar interface being constructed.

An evaluation was performed for 8 test subjects, which revealed that determination was possible with a distinction ratio (a rate of correct results of determination within the total number of trials) of 81.3%.

However, an electroencephalogram measurement must be performed by using an electrode which is worn at the parietal as mentioned above. Therefore, in the case where a device which does not have a structure to come in contact with the parietal (e.g., the aforementioned HMD) is used, it is necessary to separately wear an electrode for measuring an electroencephalogram on the parietal. An HMD is a device which is not worn at all times but is worn only when necessary, and is frequently attached or detached. Therefore, it would be a burden on the user to separately wear any electrode other than the HMD. This circumstance is also true of any device other than HMDs that does not have a structure to come in contact with the parietal.

Studies of acquiring a biological signal of a user by using an HMD are under way. For example, Japanese Laid-Open Patent Publication No. 7-64709 discloses a method in which an electrode is provided at a position on the inside of an HMD where the electrode comes in contact with the face of a user; an electro-oculographic potential and an electromyogram are measured; and a direction of a line of sight is detected. Japanese Laid-Open Patent Publication No. 9-38037 discloses a method in which electrodes are attached at up, down, right, and left positions of an eye and an electro-oculographic potential is measured by measuring potential differences between them. All of these are studies of measuring a response of a facial muscle (electromyogram) or an eyeball motion (electro-oculographic potential).

SUMMARY OF THE INVENTION

An objective of the present invention is to provide an electroencephalogram interface which, without measuring an electroencephalogram at the Pz position (median parietal) according to the International 10-20 system, operates with a similar accuracy to that of any electroencephalogram interface system which operates based on an electroencephalogram measured at the Pz position, this being made possible by employing a novel electrode position in conjunction with the facial electrodes which have been conventionally employed for measurements of an electro-oculographic potential, an electromyogram, etc., the novel electrode position being within the range of a wearable device shape such as an HMD.

A control method for a device utilizing an electroencephalogram according to the present invention comprises: step (a) of presenting a visual stimulation concerning a manipulation menu for a device; step (b) of measuring a plurality of event-related potentials after the visual stimulation is presented, where a plurality of event-related potentials based on a timing of presenting the visual stimulation as a starting point are measured from a potential difference between each of a plurality of electrodes worn on a face of a user and at least one reference electrode worn in an ear periphery of the user; step (c) of, from each of the plurality of measured event-related potentials, extracting electroencephalogram data which is at 5 Hz or less and contains a predetermined time section, and combining the extracted electroencephalogram data into electroencephalogram characteristic data; step (d) of comparing the electroencephalogram characteristic data against reference data, the reference data being prepared in advance for determining a desire to select an item in the manipulation menu; and step (e) of, based on a result of comparison of step (d), executing a manipulation of the device corresponding to the item in the manipulation menu.

The predetermined time section may be a time section from 200 ms to 400 ms based on the presenting of the visual stimulation as a starting point.

Step (b) may measure the plurality of event-related potentials by using at least one reference electrode worn in each one of two ear peripheries of the user.

Step (b) may measure the plurality of event-related potentials by using an electrode worn in at least one of a position above a right eye and a position above a left eye of the user.

Step (c) may extract, from waveforms of the plurality of measured event-related potentials, electroencephalogram characteristic data representing characteristic features of the waveforms in terms of time and frequency.

Step (c) may subject the measured waveforms of the electroencephalograms to a wavelet transform to extract electroencephalogram characteristic data representing characteristic features of the waveforms in terms of time and frequency.

Step (c) may extract electroencephalogram characteristic data representing characteristic features in a time section from 200 ms to 400 ms after presenting the manipulation menu for the device at step (a) and at frequencies of 5 Hz or less.

Step (c) may extract, from waveforms of the plurality of event-related potentials measured with the at least one reference electrode in the ear periphery and the plurality of electrodes on the face, data representing a characteristic feature of each waveform, and generate a single piece of electroencephalogram characteristic data based on the respective data.

The control method may further comprise: step (f) of, based on electrical characteristics between each of the plurality of electrodes worn on the face of the user and the at least one reference electrode worn in each one of two ear peripheries of the user, determining a state of attachment of each of the plurality of electrodes and the at least one reference electrode; and step (g) of, based on a result of determination of step (f), determining a combination of electrodes for measuring the plurality of event-related potentials at step (b).

Step (g) may detect, among combinations of electrodes obtained by respectively combining a plurality of electrodes worn on the face of the user and the at least one reference electrode worn in each one of two ear peripheries of the user, a plurality of combinations of electrodes of which measured values of the plurality of event-related potentials each exceed a threshold value, and search for an electrode which is commonly included among the plurality of combinations of electrodes to identify an electrode whose state of attachment is insufficient.

The electrode identified at step (g) may be notified in a distinguishable manner.

An electroencephalogram interface system according to the present invention comprises: an output section for visually presenting a manipulation menu; a plurality of electrodes respectively worn in an ear periphery and on a face of a user for measuring electroencephalograms of the user; an electroencephalogram characteristic extraction section for extracting electroencephalogram data which is at 5 Hz or less and contains a predetermined time section from each of a plurality of event-related potentials measured from potential differences between a plurality of electrodes worn on the face and at least one reference electrode worn in the ear periphery based on a timing of presenting the manipulation menu as a starting point, and combining the extracted electroencephalogram data into electroencephalogram characteristic data representing characteristic features of waveforms of the plurality of measured event-related potentials; and a determination section for determining a similarity level by comparing the electroencephalogram characteristic data against reference data which is prepared in advance for determining a desire to select an item in the manipulation menu, and controlling a device based on a result of determination.

The output section may be a display; and the determination section may control a displayed substance on the display based on the result of determination.

The electroencephalogram interface system may further comprise a transmission section for outputting a control signal for an external device, wherein the determination section outputs the control signal based on the result of determination, and controls an operation of the external device based on the control signal.

A control device according to the present invention is a control device for a display device, the control device and the display device together constituting an electroencephalogram interface system, the control device comprising: a communication section for communicating with the display device to cause the display device to visually present a manipulation menu; a plurality of electrodes respectively worn in an ear periphery and on a face of a user for measuring electroencephalograms of the user; an electroencephalogram characteristic extraction section for extracting electroencephalogram data which is at 5 Hz or less and contains a predetermined time section from each of a plurality of event-related potentials measured from potential differences between a plurality of electrodes worn on the face and at least one reference electrode worn in the ear periphery based on a timing of presenting the manipulation menu as a starting point, and combining the extracted electroencephalogram data into electroencephalogram characteristic data representing characteristic features of waveforms of the plurality of measured event-related potentials; and a determination section for determining a similarity level by comparing the electroencephalogram characteristic data against reference data which is prepared in advance for determining a desire to select an item in the manipulation menu, and controlling a device based on a result of determination.

According to the present invention, by using a device having a plurality of electrodes at positions in contact with the user, including his or her face, an electroencephalogram interface system is constructed which operates with an accuracy similar to that of a conventional electroencephalogram interface system which is based on an electroencephalogram measurement at the parietal. Such a device may be a device which is to be worn in a relatively narrow range on the head of the user, e.g., an eyeglasses (goggles)-type HMD, on which electrodes corresponding to the face and ears of the user may be provided. This makes it unnecessary for the user to wear any electrodes at positions other than positions where the device comes in contact with the user, such that electrode wearing is accomplished simultaneously with the wearing of the HMD, whereby the burden of device wearing is reduced.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 3 is a diagram showing a relationship between all electrode position combinations and distinction ratios as a result of an experiment performed by the inventors.

FIG. 6 is a diagram showing a relationship between electrode combinations and distinction ratios.

Figure 13:
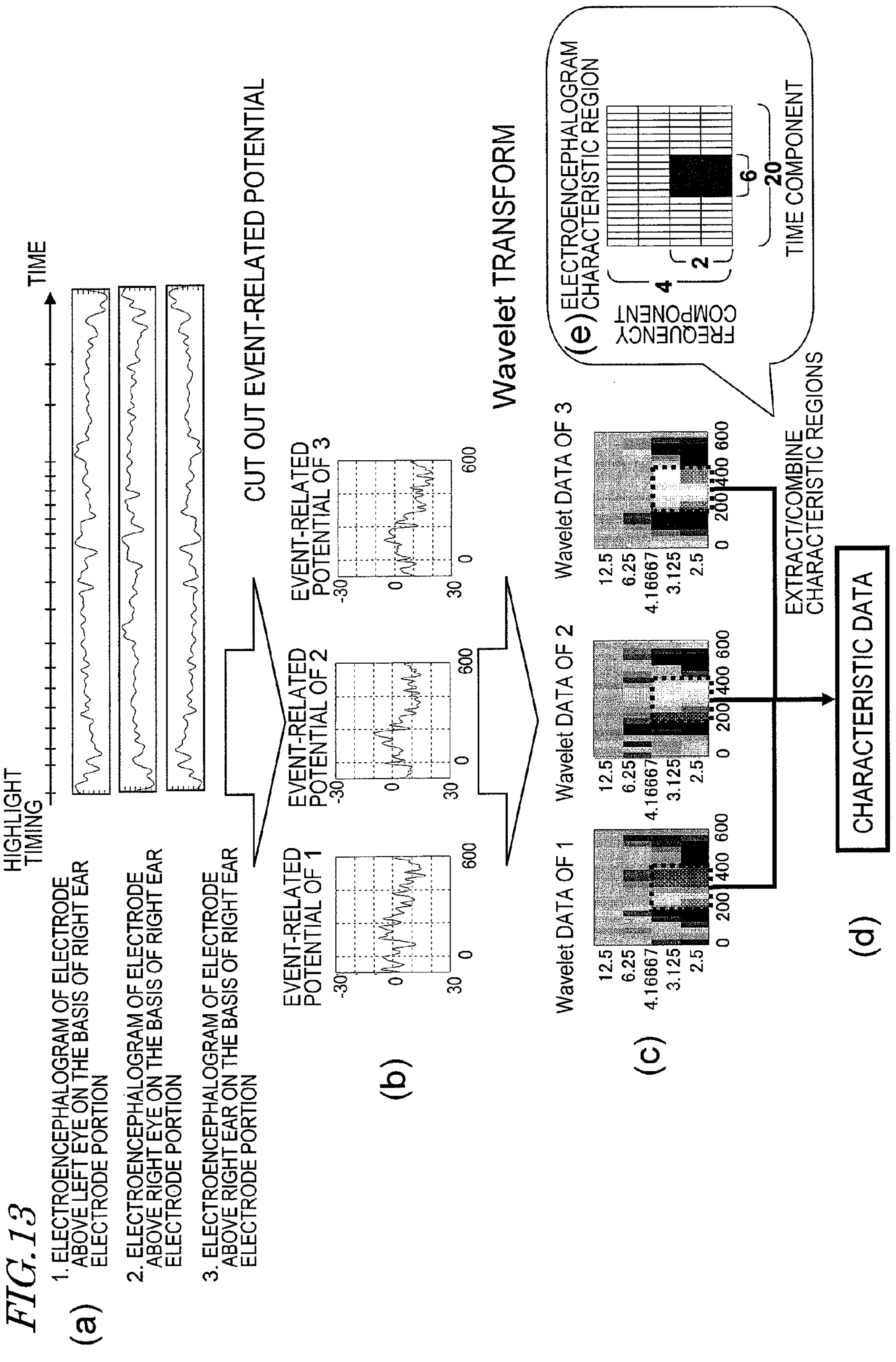

Portions (a) to (e) of FIG. 13 are diagrams showing transitions in a process of extracting characteristic data from an electroencephalogram waveform measured at each electrode.

Figure 14:
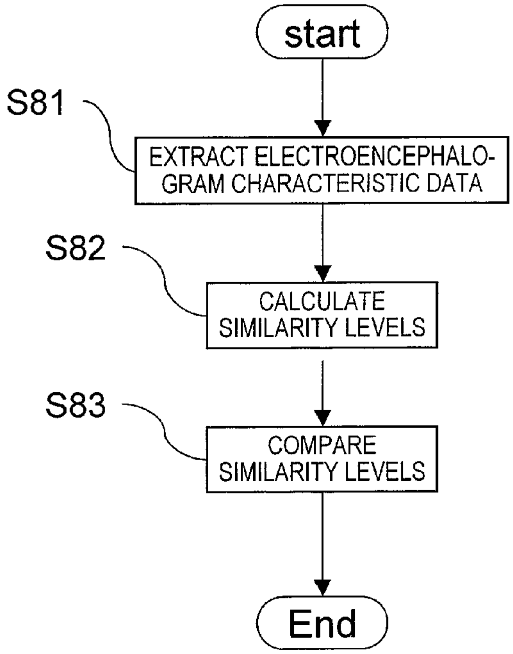

FIG. 14 is a flowchart of processing by a determination section 14.

Figure 15:
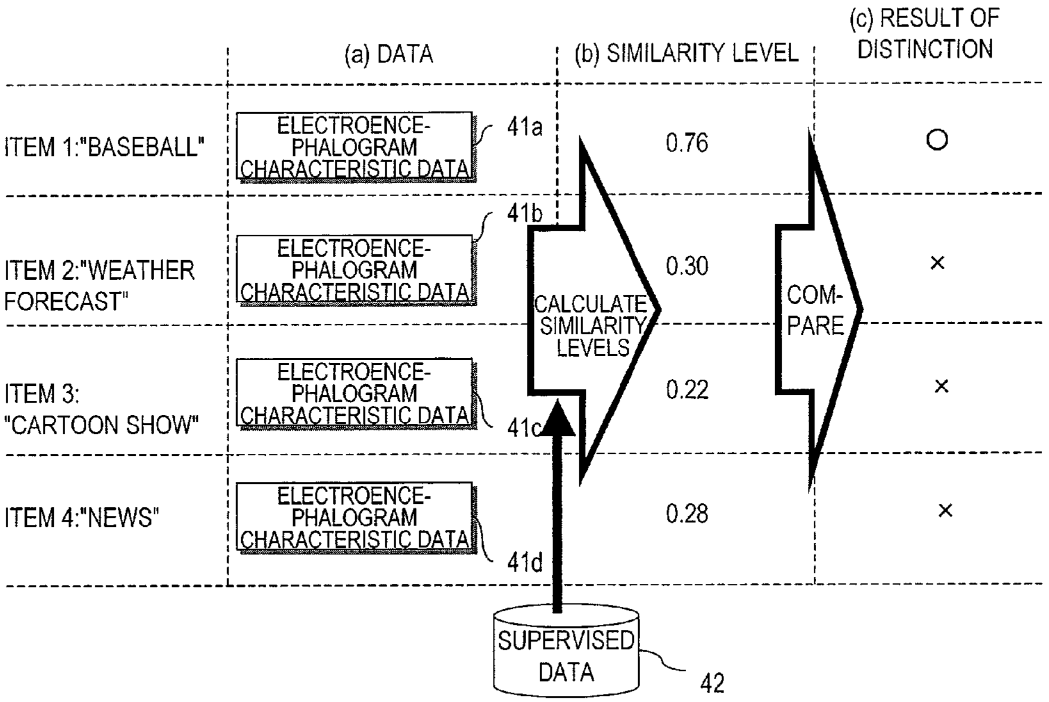

FIG. 15 is a diagram showing an order of processing by the determination section 14.

Figure 16:
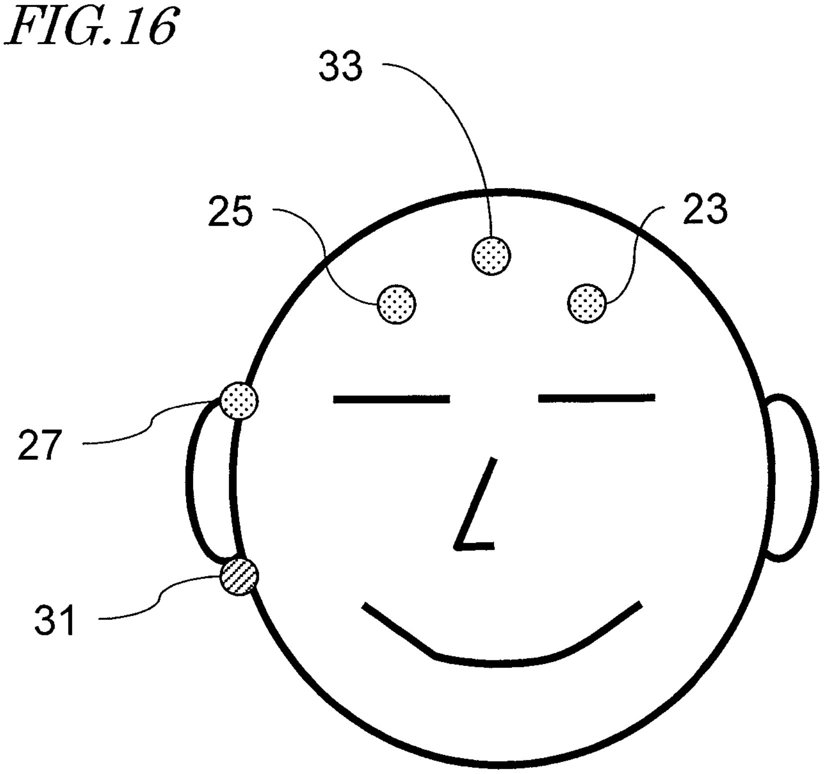

FIG. 16 is a diagram showing examples of positions which are in contact with the face of a user 10 in the present experiment in which an HMD-type electroencephalogram interface system 1 is used.

FIG. 17 is a diagram showing an example of supervised data.

Figures 18, 19:
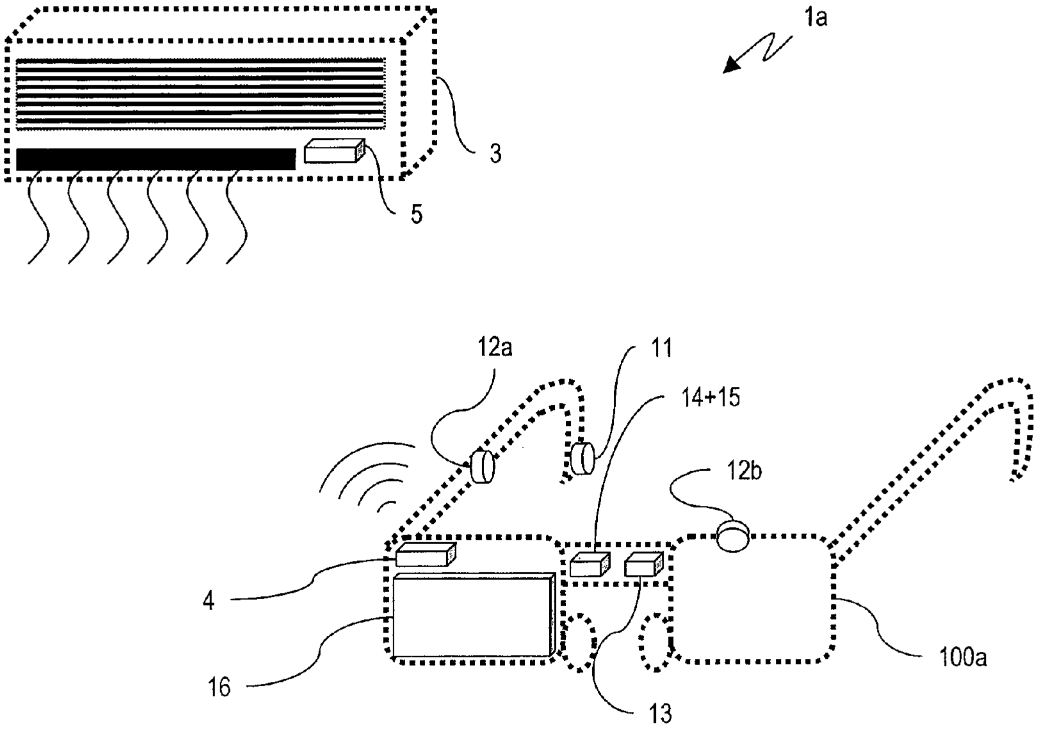

FIG. 18 is a diagram showing results of accuracy checks.

FIG. 19 is a diagram showing an electroencephalogram interface system 1*a* according to a first variant of Embodiment 1.

Figure 20:
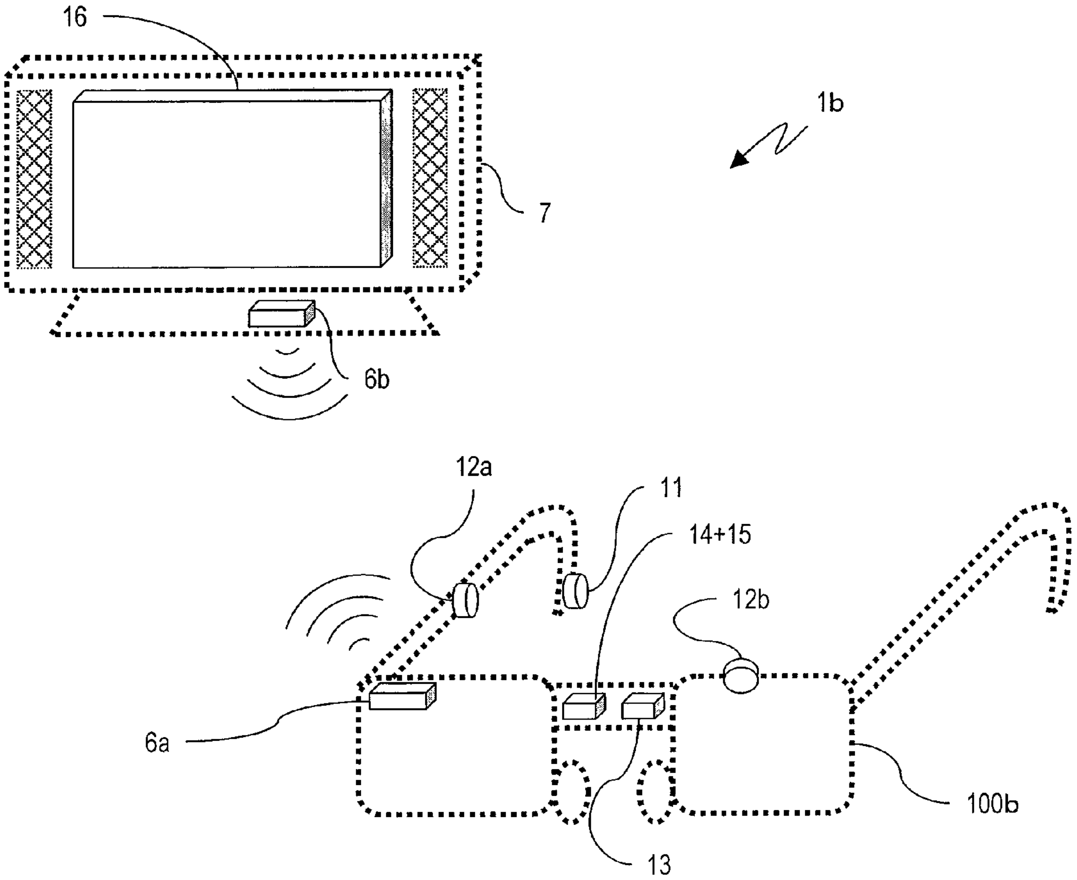

FIG. 20 is a diagram showing an electroencephalogram interface system 1*b* according to a second variant of Embodiment 1.

Figure 21:
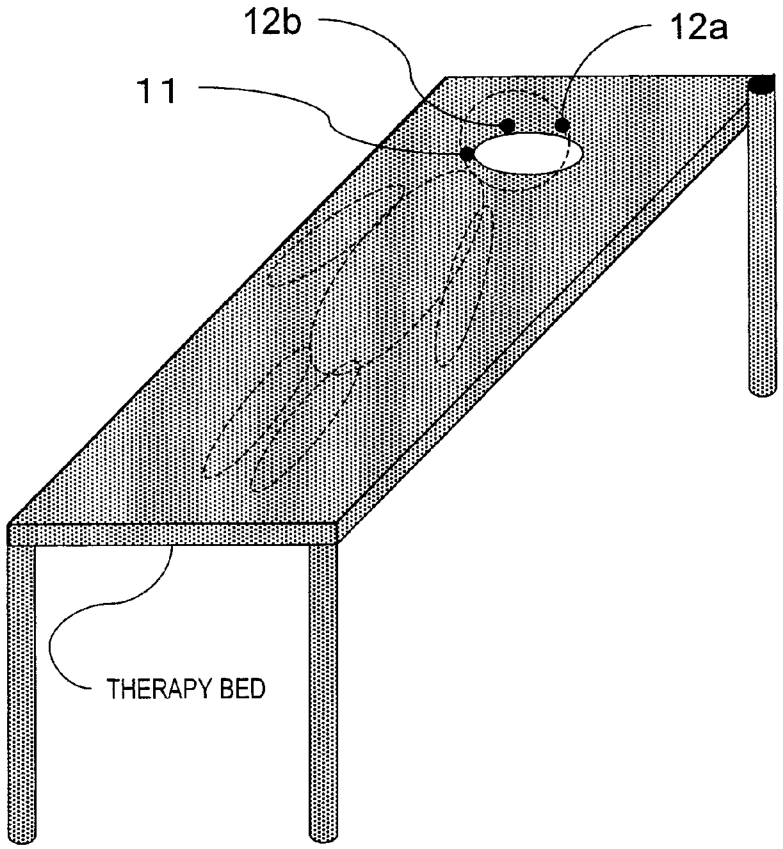

FIG. 21 is a diagram showing an example of a therapy bed for massaging, as an example other than HMDs.

Figure 22:
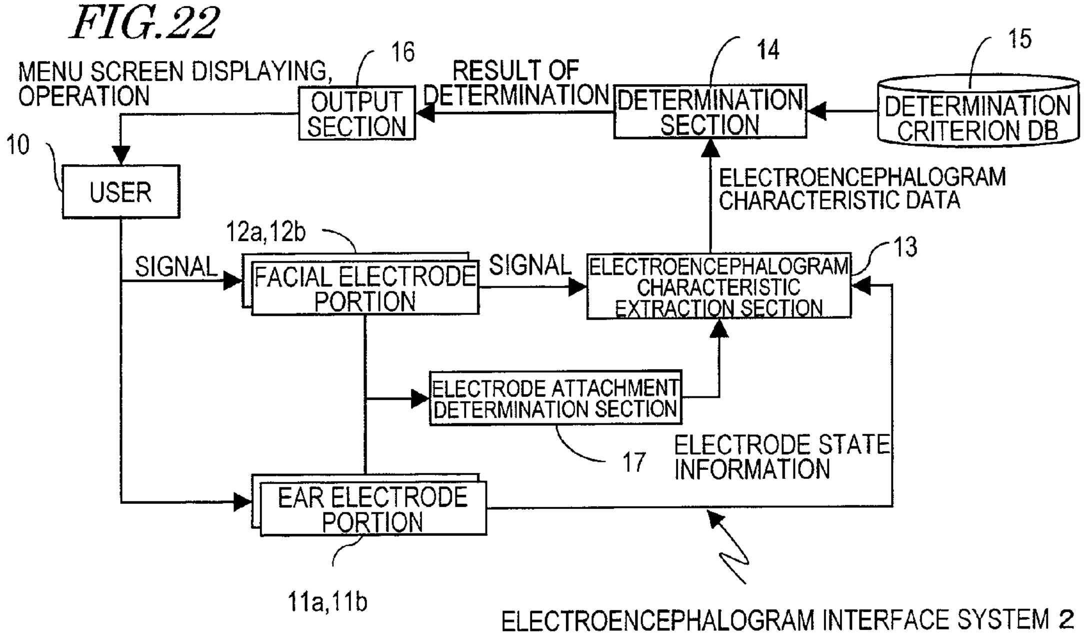

FIG. 22 is a construction diagram showing an electroencephalogram interface system 2 according to an embodiment.

Figure 23:
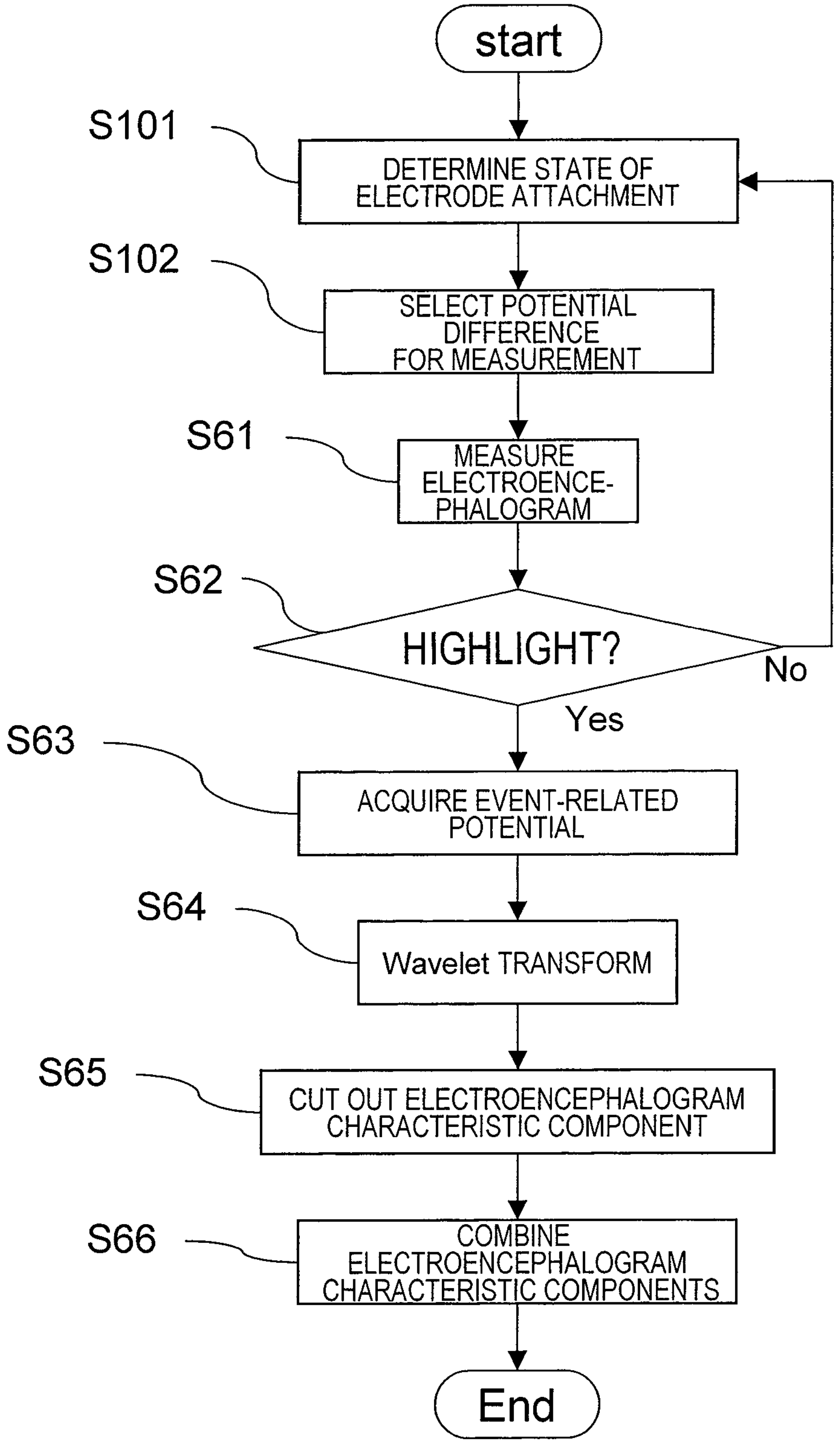

FIG. 23 is a flowchart of an electroencephalogram characteristic data extraction process in an electroencephalogram characteristic extraction section 13.

Figure 24:
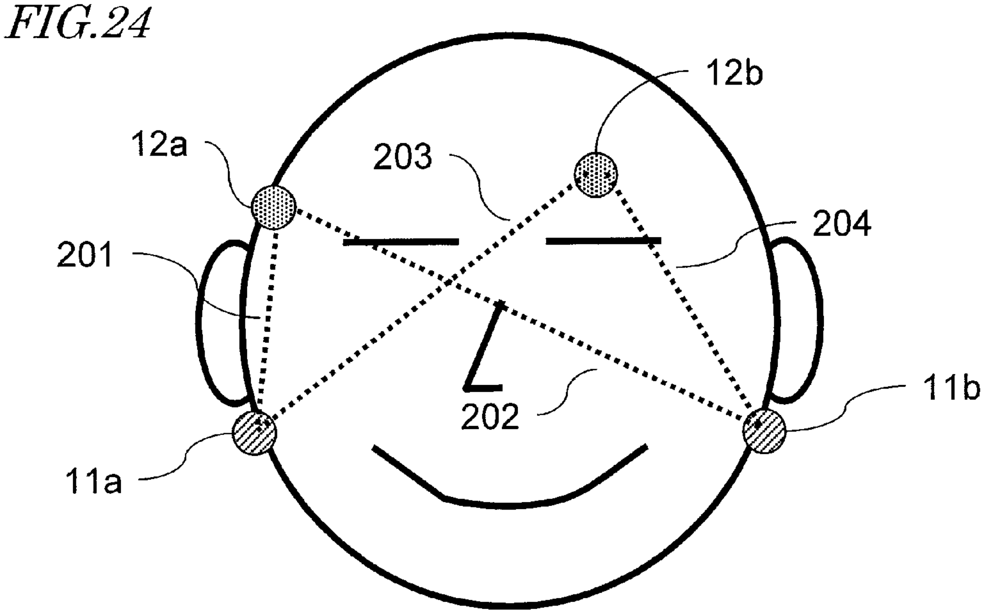

FIG. 24 is a diagram showing positions at which electrodes are worn.

Figure 25:
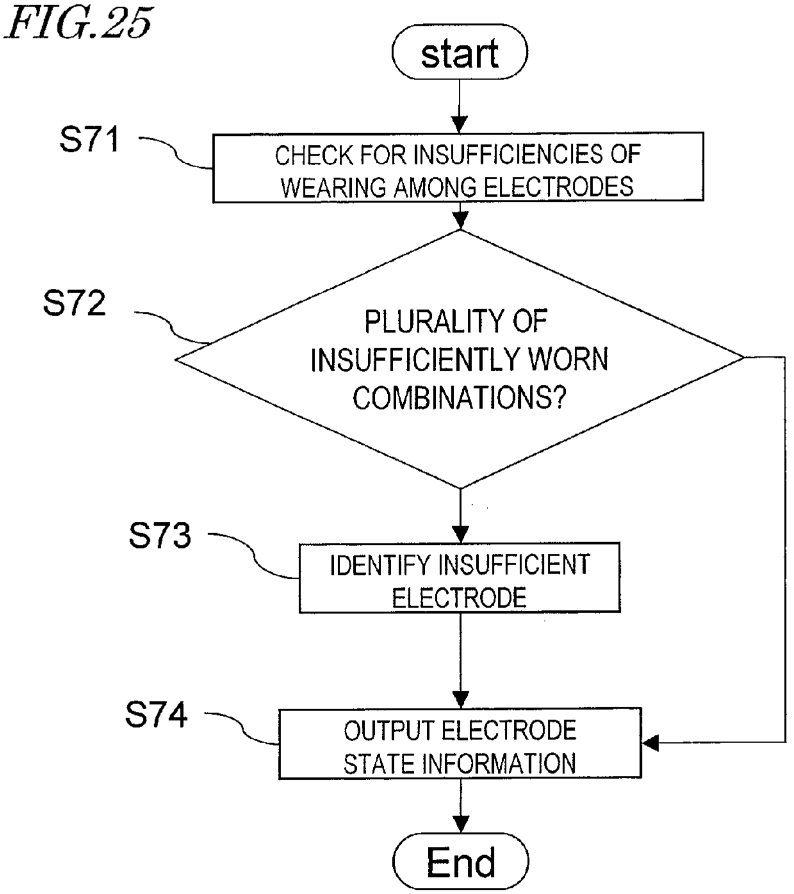

FIG. 25 is a flowchart of processing by an electrode attachment determination section 17.

Figure 26A:
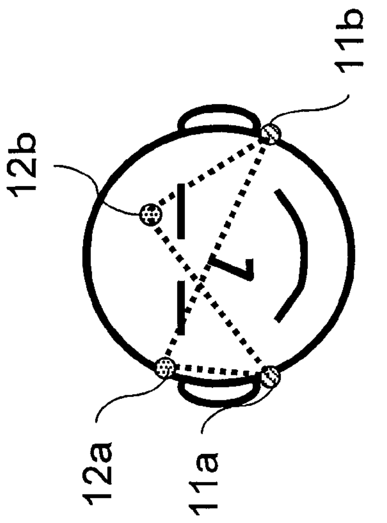
Figure 26B:
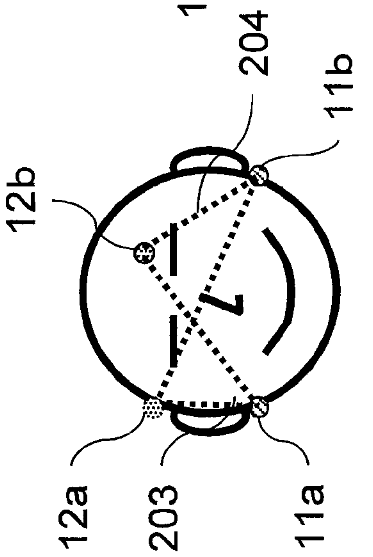
Figure 26C:
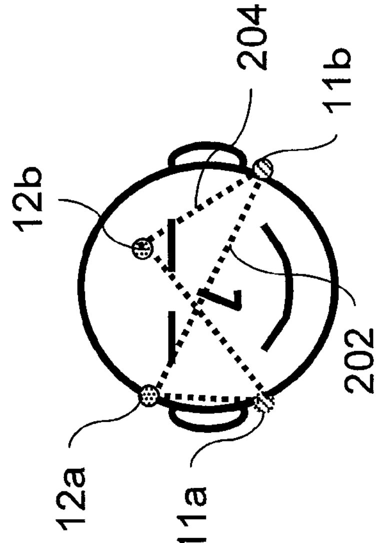

FIGS. 26A to 26C are diagrams showing exemplary electrodes used for measurements of respective states of electrode attachment.

Figures 27, 28:
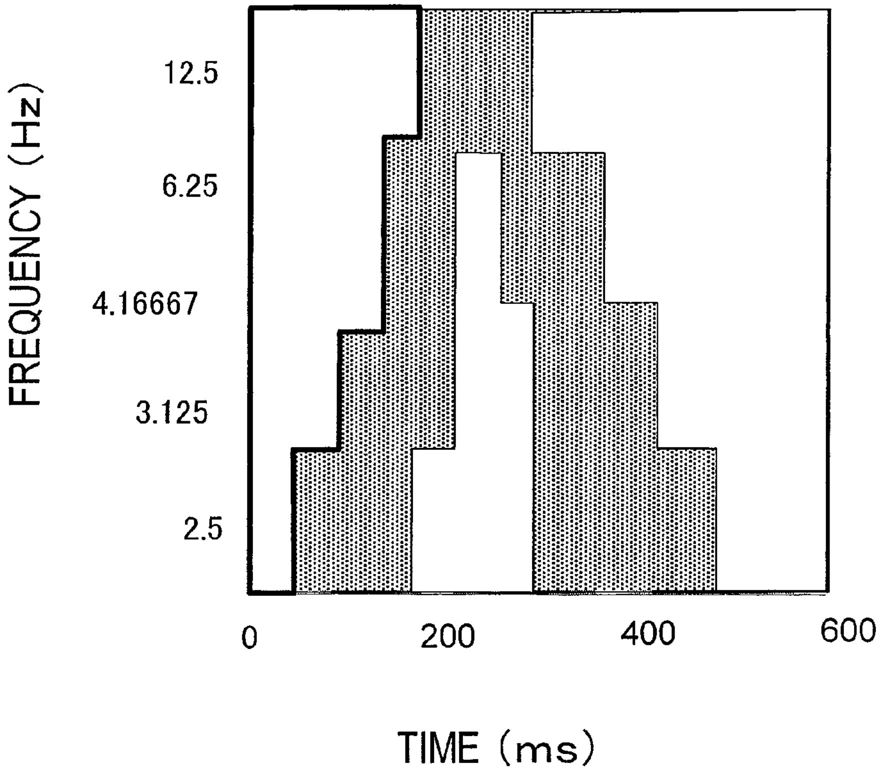

FIG. 27 is a diagram showing results of accuracy checks.

FIG. 28 is a diagram showing an example of an occurrence time slot and frequency band of a characteristic signal occurring at the parietal.

Figure 29:
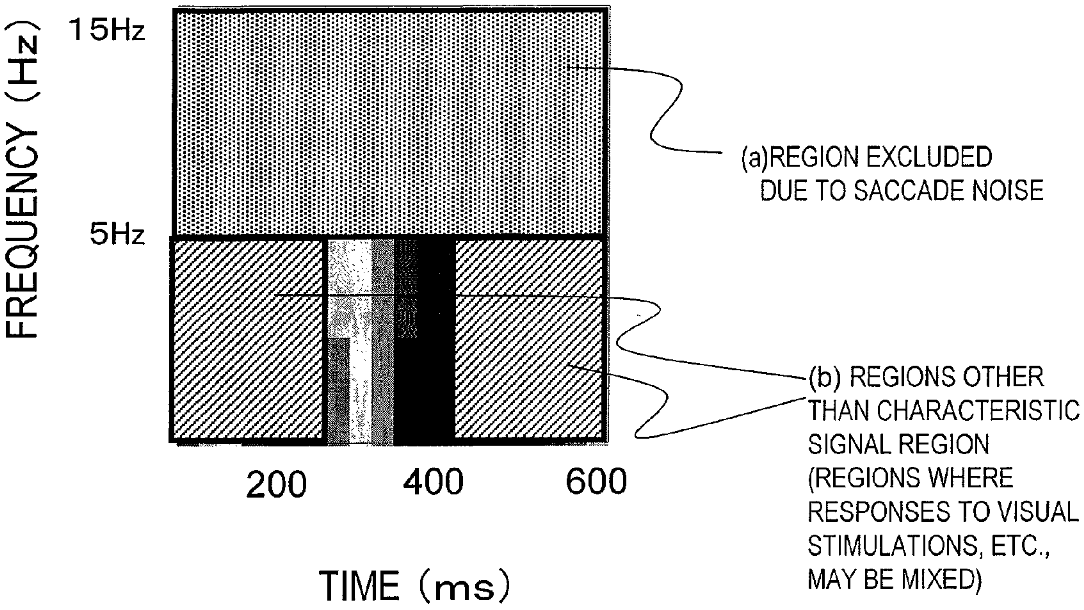

FIG. 29 is a diagram showing a region in wavelet-transformed data to be cut out.

DETAILED DESCRIPTION OF PREFERRED EMBODIMENTS

Hereinafter, preferred embodiments of the present invention will be described with reference to the accompanying drawings.

Hereinafter, an experiment which has been performed by the inventors will be described first. Then, a finding which has been derived through the experiment will be described, specifically: an electroencephalogram interface can be constructed which, without measuring an electroencephalogram at the Pz position (median parietal) according to the International 10-20 system, operates with a similar accuracy to that of any electroencephalogram interface system which operates based on an electroencephalogram measured at the Pz position, this being made possible by employing facial electrodes that have conventionally been employed for measurements of an electro-oculographic potential, an electromyogram, etc., as well as another electrode which is provided at a position that comes in contact with the user. Thereafter, respective embodiments of the electroencephalogram interface will be described.

As described earlier, there have been conventional studies to provide electrodes at positions on a head-mount display (HMD) that come in contact with the face of a user and measure a response of a facial muscle (electromyogram) or an eyeball motion (electro-oculographic potential).

The inventors have conducted an experiment in which electrodes are provided at positions on an HMD that come in contact with the face of a user to see whether an electroencephalogram can be measured by using such electrodes.

In the experiment, the inventors constructed an electroencephalogram interface, measured electroencephalograms of 8 test subjects with an electrode provided at the Pz (median parietal), and evaluated the electroencephalogram interface based on the electroencephalograms. In addition, the inventors constructed an electroencephalogram interface for measuring an electroencephalogram by employing electrode positions that are employed in conventional electro-oculographic potential measurement, and evaluated that electroencephalogram interface with respect to the same 8 test subjects.

Figure 1:
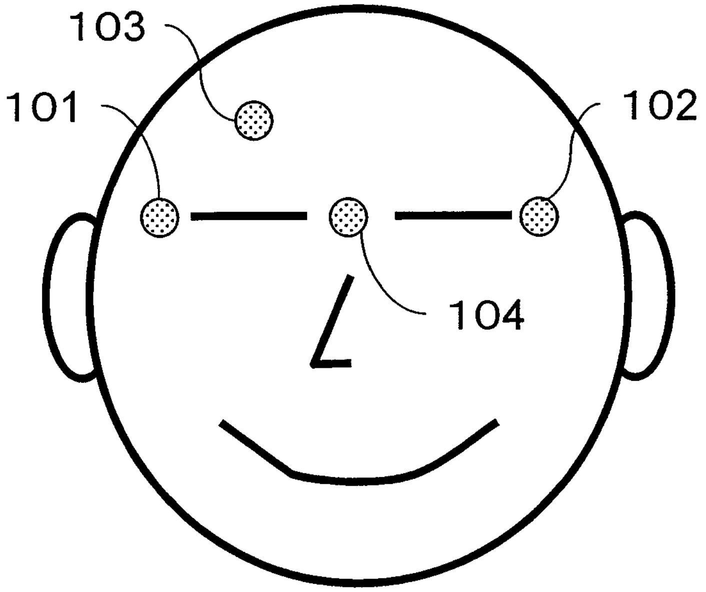
FIG. 1 is a diagram showing positions 101 to 104 of electrodes employed in conventional electro-oculographic potential measurement.

FIG. 1 shows positions 101 to 104 of electrodes employed in conventional electro-oculographic potential measurement. The electrodes are attached at positions 101 and 102 on the right and left of the eyes of a user, a position 104 between both eyes, and a position 103 above the right eye.

In a method of measuring an electroencephalogram, in each electrode combination, one electrode is used as a reference electrode and the other electrode is used as a measurement electrode, and the potential of the measurement electrode is measured on the basis of the reference electrode. The electroencephalogram interface makes a determination by utilizing this measured electroencephalogram.

In the present experiment, in the electrode combinations conventionally used for electro-oculographic potentials, one electrode was defined as the reference electrode and the other was defined as the measurement electrode. Thus, a distinction ratio evaluation was performed.

The results of the evaluation are as follows:

a distinction ratio when performing a measurement at positions for measuring right-left motions of the eyes (a potential difference between a reference electrode, which is "alongside the right eye" 101, and a measurement electrode, which is "alongside the left eye" 102)=37.8%; and a distinction ratio when performing a measurement at positions for measuring up-down motions of the eyes (reference electrode: "above the right eye" 103; measurement electrode: nose 104)=63.8%.

It can be seen that, in comparison with the distinction ratio obtained by measuring an electroencephalogram at Pz, the accuracy obtained at the conventionally-employed electrode positions is poor.

In an electro-oculographic potential measurement, which aims to measure a potential occurring at the portion(s) where the electrode(s) is worn, the relative positioning of electrodes is important. However, in the measurement of an electroencephalogram, a potential occurring at the parietal is to be measured somewhere on the face, and there is no need to limit the relative positioning of electrodes to the relative positioning of the conventional electro-oculographic potential measurement.

Figure 2:
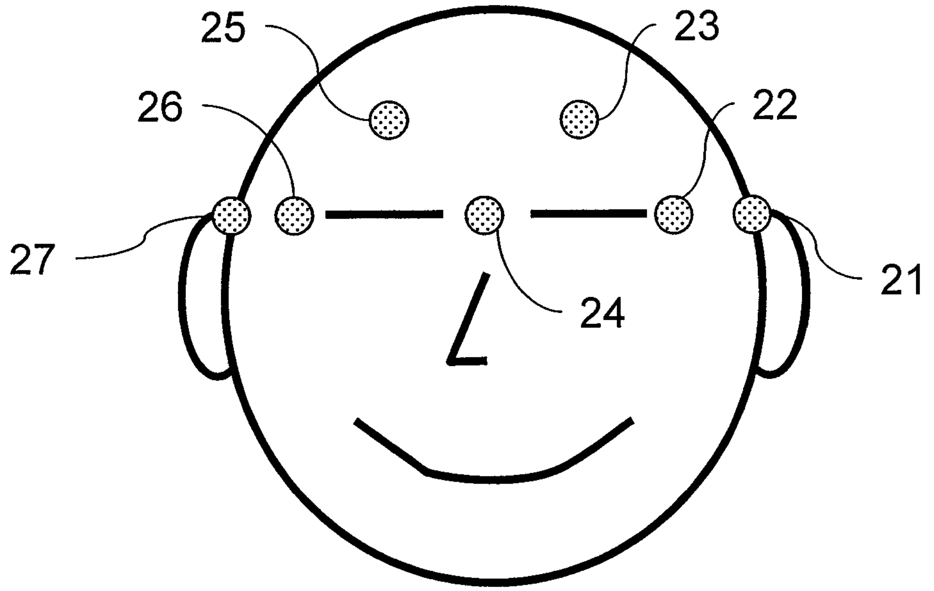
FIG. 2 is a diagram showing, among electrode positions conventionally employed in electro-oculographic potential measurement and electromyographic measurement, electrode positions that are contained within the range of an HMD shape.

Therefore, within a range in which an HMD would come in contact with the head of a user (hereinafter expressed as "within the range of an HMD shape"), combinations of electrode positions which are conventionally employed in electro-oculographic potential/electromyographic measurements were exhaustively sought; an electroencephalogram interface was constructed; and a distinction ratio evaluation was made. FIG. 2 shows, among electrode positions conventionally employed in electro-oculographic potential measurement and electromyographic measurement, electrode positions that are contained within the range of an HMD shape. Contemplated as electrode positions are: above the right ear 21, alongside the right eye 22, above the right eye 23, nose 24, above the left eye 25, alongside the left eye 26, and above the left ear 27.

The inventors explored all pairs, where each pair consisted of two electrodes among the electrodes which can be provided at the positions 21 to 27 on the face as shown in FIG. 2. Then, by defining one electrode as the reference electrode and the other electrode as the measurement electrode, a distinction ratio evaluation was performed for the electroencephalogram interface. FIG. 3 shows the relationship between all electrode position combinations and distinction ratios.

According to the results of the experiment, when any facial electrodes were combined, the distinction ratio could only be as large as 65.9%, which was obtained by utilizing a potential difference between an electrode alongside the right eye 26 and the reference electrode above the right eye 25.

It was thus concluded that, when an item selected by a user is determined through an electroencephalogram measurement which is made only with electrodes that are on the front part of the face, the resultant accuracy will be poor, as compared to the distinction ratio of 81.3% which is obtained through a measurement at the Pz position, indicative of an insufficient performance of the electroencephalogram interface.

Next, an experiment which was performed by the inventors to search for optimum reference electrode positions within the range of an HMD shape will be described.

Figure 4A:
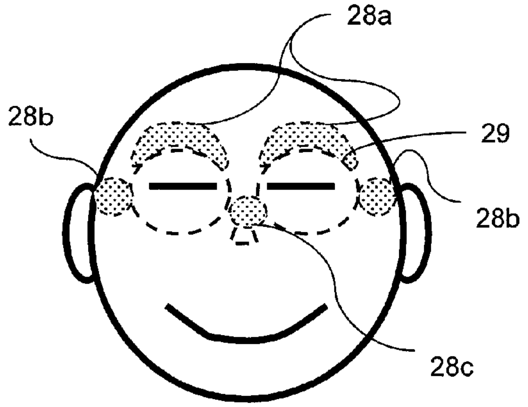
FIG. 4A is a diagram showing facial electrode positions.

FIG. 4A shows facial electrode positions which are employed in conventional electro-oculographic potential measurement. As shown in FIG. 4A, electrodes "above the eyes" 28*a* are worn at the upper edges of eye sockets 29; electrodes "alongside the eyes" 28*b* are worn at the outer edges of the eye sockets 29 (outer corners of the eye lids); and a nose electrode is worn at the nasion 28*c*.

Figure 4B:
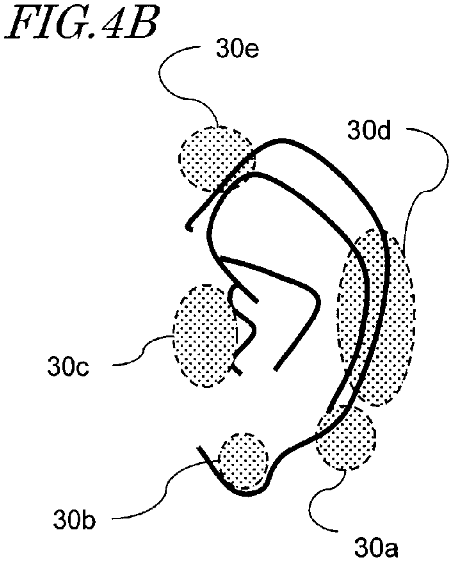
FIG. 4B is a diagram showing electrode positions in an ear periphery.

FIG. 4B shows electrode positions 30*a* to 30*e* in an ear periphery. In conventional electro-oculographic potential measurement, electrodes are also worn at ear root upper portions 30*e*, which are above the ears.

In view of the range of an HMD shape, in addition to the facial electrodes which are employed in electro-oculographic potential measurement, it is possible to provide further electrodes in positions at which the HMD will come in contact with the ears. Specifically, these positions are in the ear periphery, e.g., mastoids 30*a* at the infraotics (under the ear roots), earlobes 30*b*, tragi 30*c* at the prootics, and opisthotics (behind the ear roots) 30*d*. As a representative of the aforementioned ear periphery, the inventors have chosen the mastoids 30*a*, which are protrusions of the cranium at the hind roots of the ears, and conducted an experiment of evaluating the distinction ratio of an electroencephalogram interface for the conventionally-employed electrode positions on the face, relative to reference electrodes at the mastoids.

For the experiment, positions shown in FIG. 2 were used as exemplary positions within an HMD shape that are in contact with the face of a user, and a specific study of accuracy was performed by utilizing these portions.

In the experiment, a measurement experiment was performed for 15 test subjects in their twenties, among whom test subjects that maintained a high arousal level were subjected to analysis.

As for the electroencephalogram measurement, Polymate AP-1124 (manufactured by DIGITEX LAB. CO., LTD) was used, with a sampling frequency of 200 Hz and a time constant of 3 seconds, and with a 30 Hz low-pass filter being used for filtering.

Figure 5:
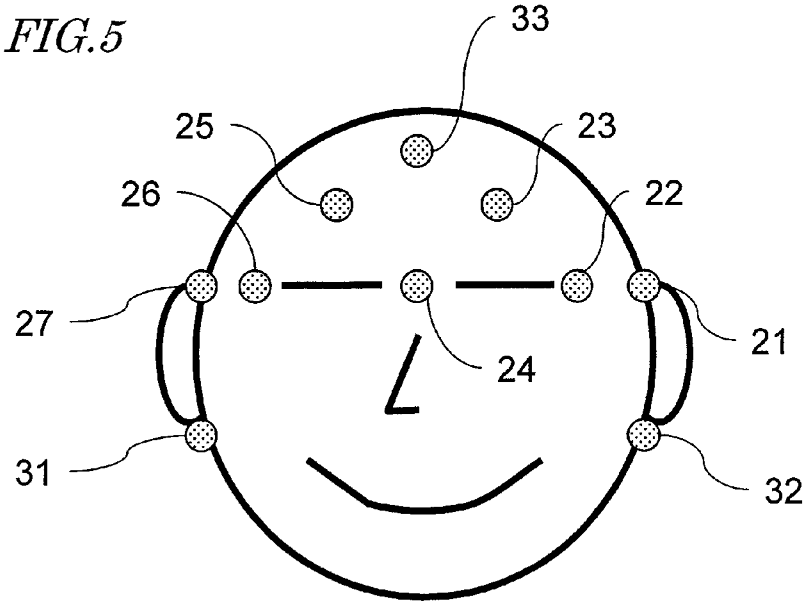
FIG. 5 is a diagram showing exemplary electrode positions in an experiment performed by the inventors.

FIG. 5 shows exemplary electrode positions in this experiment. In this experiment, a reference electrode was placed at either the right mastoid 31 or the left mastoid 32. As the facial electrode portions, electrodes were worn at the seven positions which are conventionally used for electro-oculographic potential and electromyographic measurement, i.e., above the right ear 21, alongside the right eye 22, above the right eye 23, the nose 24, above the left eye 25, alongside the left eye 26, and above the left ear 27. A ground electrode was worn at FPz33 according to the position notation of the International 10-20 system. Each test subject was asked to make 40 selections, and the rate at which correct results of determination were obtained was calculated as the distinction ratio, thus performing an accuracy check.

FIG. 6 shows a relationship between electrode combinations and distinction ratios. It was found from the experimental results that, among the combinations in which the reference electrode was on a mastoid, a potential difference of the position above the right eye on the basis of the reference electrode at the right mastoid 31 provided the highest distinction ratio of 75.3%. On average, too, the distinction ratios were 57.8% on the basis of the left mastoid, and 66.6% on the basis of the right mastoid. This indicates that an electroencephalogram obtained by measuring a facial potential on the basis of the right or left mastoid provides a higher distinction ratio than that of an electroencephalogram measured on the basis of any facial electrode, and contains an electroencephalogram signal that is necessary for constructing an electroencephalogram interface.

Thus, by measuring an electroencephalogram by utilizing a potential difference of a facial electrode on the basis of an ear periphery (mastoid), the distinction ratio can be improved by about 10% over the case where an electroencephalogram is measured by only using facial electrodes.

However, even when an electroencephalogram is measured by utilizing a potential difference of a facial electrode on the basis of a mastoid, the maximum distinction ratio is 75.3%, which still falls short of the distinction ratio of 81.3% obtained by utilizing Pz.

Next, the inventors measured an event-related potential by utilizing a facial potential on the basis of an ear periphery, and made a determination by utilizing data of a frequency band in which an electroencephalogram signal occurring in the neighborhood of the parietal (Pz) is contained.

The specific determination method will be described. First, a measured event-related potential is subjected to a time-frequency decomposition (which in the present embodiment is a wavelet transform) in order to extract an occurrence time slot and a frequency band of a characteristic signal of the electroencephalogram when making a selection. An example of an occurrence time slot and frequency band of a characteristic signal occurring at the parietal is shown in FIG. 28. FIG. 28 shows time (unit: ms) on the horizontal axis and frequency (unit: Hz) on the vertical axis. A time-frequency domain which is shown hatched in FIG. 28 is a characteristic signal that is utilized for the determination of an event-related potential which is measured at the parietal. At any portion on the face as well, similarly, regions other than the characteristic signal were excluded, and only the characteristic signal region of FIG. 28 was extracted was subjected to determination. The resultant accuracy was 69.7%, which was lower than 75.3%. This is considered to be because a large amount of noise was mixed in the region of a weak signal.

Thus, in order to obtain a further improved accuracy, after excluding regions in which noises (due to e.g., blinks) may be mixed, the inventors have extracted a time-frequency domain of a weak characteristic signal which is a result of an electroencephalogram signal occurring in the neighborhood of the parietal and having propagated to the front part of the face, and combined a plurality of components thereof. As a result, an intense characteristic signal which is necessary for an electroencephalogram interface was extracted, whereby an electroencephalogram interface having an accuracy similar to that obtained at Pz was realized. Hereinafter, this electroencephalogram interface system will be described as the present invention.

It has been confirmed according to the present invention that, with a combination of electroencephalogram signals of facial electrodes on the basis of an ear periphery, it is possible to improve the distinction ratio of an electroencephalogram interface to 80.6%, such that an electroencephalogram interface system having a sufficiently high performance can be obtained without wearing an electrode at the Pz position.

Hereinafter, with reference to the attached drawings, Embodiments of the present invention will be described.

Embodiment 1

Figure 7:
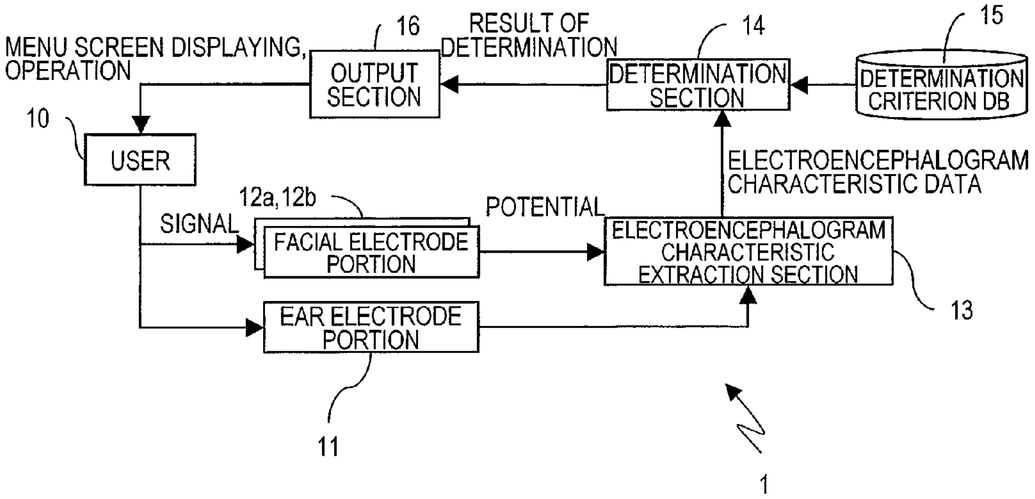
FIG. 7 is a construction diagram showing an electroencephalogram interface system 1 according to Embodiment 1.

FIG. 7 is a construction diagram of an electroencephalogram interface system 1 according to the present embodiment. The electroencephalogram interface system 1 includes an ear electrode portion 11, facial electrode portions 12, an electroencephalogram characteristic extraction section 13, a determination section 14, and a determination criterion database (DB) 15. In FIG. 7, the user 10 is illustrated for ease of understanding.

Figure 8:
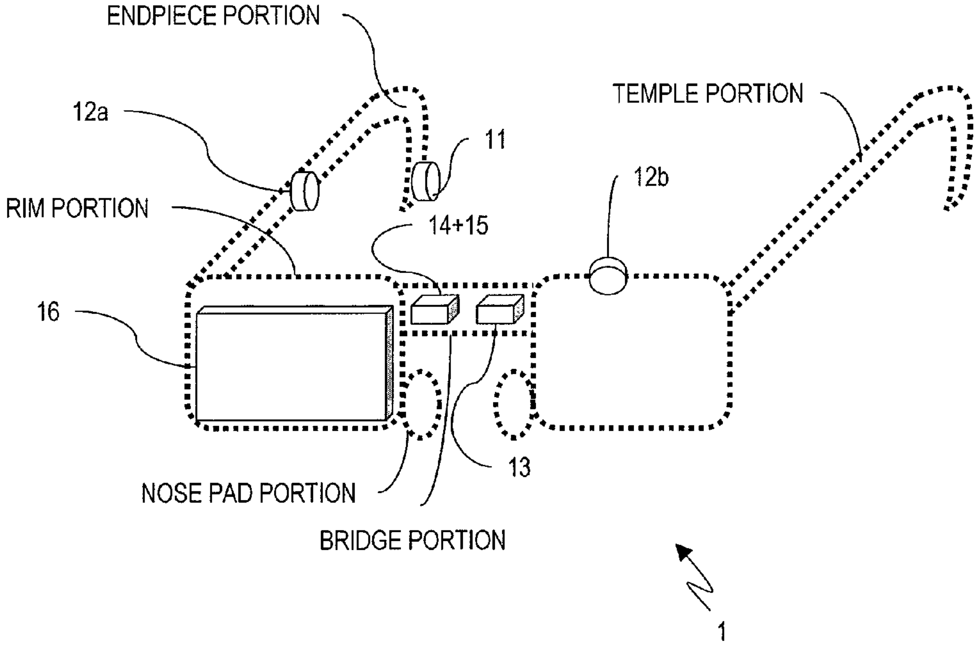
FIG. 8 is a diagram showing an Example constructing the electroencephalogram interface system 1 as an eyeglasses (goggles)-type head-mount display (HMD).

FIG. 8 illustrates an Example of constructing the electroencephalogram interface system 1 in the form of an eyeglasses (goggles)-type head-mount display (HMD). Hereinafter, the HDM-type electroencephalogram interface system 1 shown in FIG. 8 will be described in detail.

The names of respective portions of the HMD-type electroencephalogram interface system 1 shown in FIG. 8 are similar to those of eyeglasses. Hereinafter, portions which hang on the ears of the user 10 to fix the HMD main body will be referred to as "endpiece portions". Portions which come in contact with the nose of the user 10 to support the HMD main body will be referred to as "nose pad portions". A portion which supports and fixes an output section 16 which is disposed before either eyeball of the user 10 will be referred to as a "rim portion"; a portion connecting and supporting the rim portions in front of both eyes will be referred to as a "bridge portion"; and a portion connecting and supporting each rim portion and each endpiece portion will be referred to as a "temple portion".

The ear electrode portion 11 is provided in an ear periphery of the user, whereas the facial electrode portions 12*a* and 12*b* are provided in the neighborhood of the face of the user. Specifically, the ear electrode portion 11 is provided inside an endpiece portion. Thus, the ear electrode portion 11 is in contact with the neighborhood of one ear of the user 10. The facial electrode portions 12*a* and 12*b* are to be disposed on selected ones of the temple portions, rim portions, and nose pad portions of the HMD. Thus, the facial electrode portions 12*a* and 12*b* are in contact with the user at a plurality of places on the face of the user 10.

The electroencephalogram characteristic extraction section 13 measures an electroencephalogram from a difference in potential between the ear electrode portion 11 and each of the facial electrode portions 12*a* and 12*b*, and extracts electroencephalogram characteristic data. The "electroencephalogram characteristic data" represents characteristic features of an electroencephalogram in terms of time and frequency. For example, electroencephalogram characteristic data can be obtained by subjecting a measured electroencephalogram waveform to a wavelet transform described later.

From the electroencephalogram characteristic data of the user, the determination section 14 determines an item selected by the user, based on a predetermined determination criterion. The "predetermined determination criterion" is predetermined data which is stored in a determination criterion DB 15. The display 16 controls the device based on the result of determination by the determination section 14.

In the example of FIG. 8, the ear electrode portion 11 is provided inside the right endpiece of the HMD; the facial electrode portion 12*a* is provided on the right temple portion of the HMD; and the facial electrode portion 12*b* is provided on an upper part of the left rim portion of the HMD. The electroencephalogram characteristic extraction section 13, the determination section 14, and the determination criterion DB 15 are provided on the bridge portion of the HMD. The display 16 is provided on a lens portion which is in front of an eye of the user 10. Note that the display 16 is a specific example of the output section shown in FIG. 7.

The construction of FIG. 8 is only exemplary. The position of the ear electrode portion 11 may be at either the right side or the left side. The facial electrode portions 12 may be provided, in plurality, at any positions selected from the temple portions, the rim portions, the nose pad portions, and the bridge portion of the HMD. The number of facial electrode portions is not limited to the aforementioned two, i.e., 12*a* and 12*b*, but three or more electrodes may be provided in the aforementioned range, which is well within the scope of the present invention. Moreover, the positions of the electroencephalogram characteristic extraction section 13, the determination section 14, and the determination criterion DB 15 are not limited to the above; they may be disposed at any positions within the range of the HMD shape. Note that the determination criterion DB 15 does not need to be provided within the HDM, but may be disposed anywhere in the environment in which the electroencephalogram interface system 1 is used (e.g., at home); in that case, it may be connected wirelessly to the determination section 14. Alternatively, the determination criterion DB 15 may be incorporated in the determination section 14, and become a part of the function of the determination section 14.

In the above-illustrated example, the display 16 is disposed at the position of a lens of a pair of eyeglasses because outputting of a video relating to a selected item is contemplated. However, any device other than a video-displaying device may be controlled, e.g., loudspeakers for outputting audio, audio output terminals, and the like.

Figure 9:
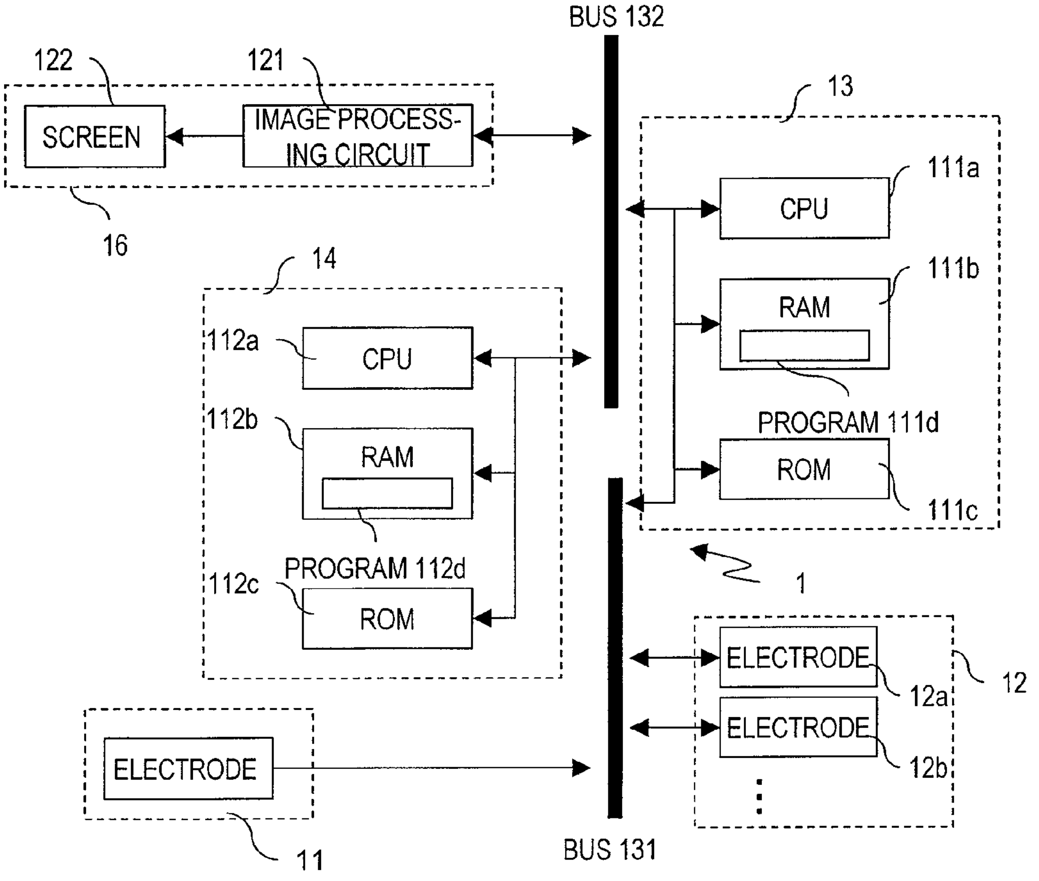
FIG. 9 is a hardware construction diagram of an electroencephalogram interface apparatus according to Embodiment 1.

FIG. 9 is a hardware construction diagram of an electroencephalogram interface apparatus according to the present embodiment.

The ear electrode portion 11 and the plurality of facial electrode portions 12 (electrodes 12*a* and 12*b*) worn on the face are connected to a bus 131, whereby exchanges of signals with the electroencephalogram characteristic extraction section 13 are performed. The electroencephalogram characteristic extraction section 13 includes a CPU 111*a*, a RAM 111*b*, and a ROM 111*c*. The CPU 111*a* reads a computer program 111*d* which is stored in the ROM 111*c* onto the RAM 111*b*, where the computer program 111*d* is laid out and executed. In accordance with the computer program 111*d*, the electroencephalogram characteristic extraction section 13 performs the processing of an electroencephalogram characteristic data extraction as described later. The electroencephalogram characteristic extraction section 13 is further connected to a bus 132, whereby exchanges of signals with various constituent elements are performed. Note that the bus 131 and the bus 132 may consist of a common bus.

The determination section 14 includes a CPU 112*a*, a RAM 112*b*, and a ROM 112*c*. The respective functions of the CPU 112*a*, the RAM 112*b*, and the ROM 112*c* are similar to those of the namesake constituent elements in the electroencephalogram characteristic extraction section 13. A computer program 112*d* stored in the ROM 112*c* performs processing based on a determination criterion in a determination criterion DB which is stored in the ROM 112*c*. For a simplified construction, the CPUs, RAMs, and ROMs of the electroencephalogram characteristic extraction section 13 and the determination section 14 may be shared, while only the computer programs are separately provided. The ROM 111*c* and the ROM 112*c* may be rewritable ROMs (e.g., EEPROMs).

The display 16 includes an image processing circuit 121. In accordance with a result from the CPU 112*a*, the image processing circuit 121 outputs a video signal, e.g., for displaying a selected content video, to a screen 122. Moreover, the display 16 may also have a function of presenting any information that is needed by the HMD.

The above display 16 is illustrated as having the image processing circuit 121 and the screen 122 because controlling of an AV device is contemplated. However, depending on the modality type of the device to be controlled, the image processing circuit 121 and the screen 122 may be replaced by an audio processing circuit, loudspeakers, and the like.

Any of the aforementioned computer programs is distributed on the market in the form of a product recorded on a storage medium such as a CD-ROM, or transmitted through telecommunication lines such as the Internet. The electroencephalogram characteristic extraction section 13 and the determination section 14 may be implemented as a piece of hardware (e.g., a DSP) consisting of semiconductor circuitry having a computer program incorporated therein.

Next, an outline of the electroencephalogram interface system 1 used as an HMD interface according to the present invention will be described. After outlining its processing, a method of extracting electroencephalogram characteristic data will be described.

An electroencephalogram interface provides an ability of, by using electroencephalogram characteristic data, distinguishing an item that a user wishes to select from among a plurality of selection items being displayed on a display or the like.

Figure 10:
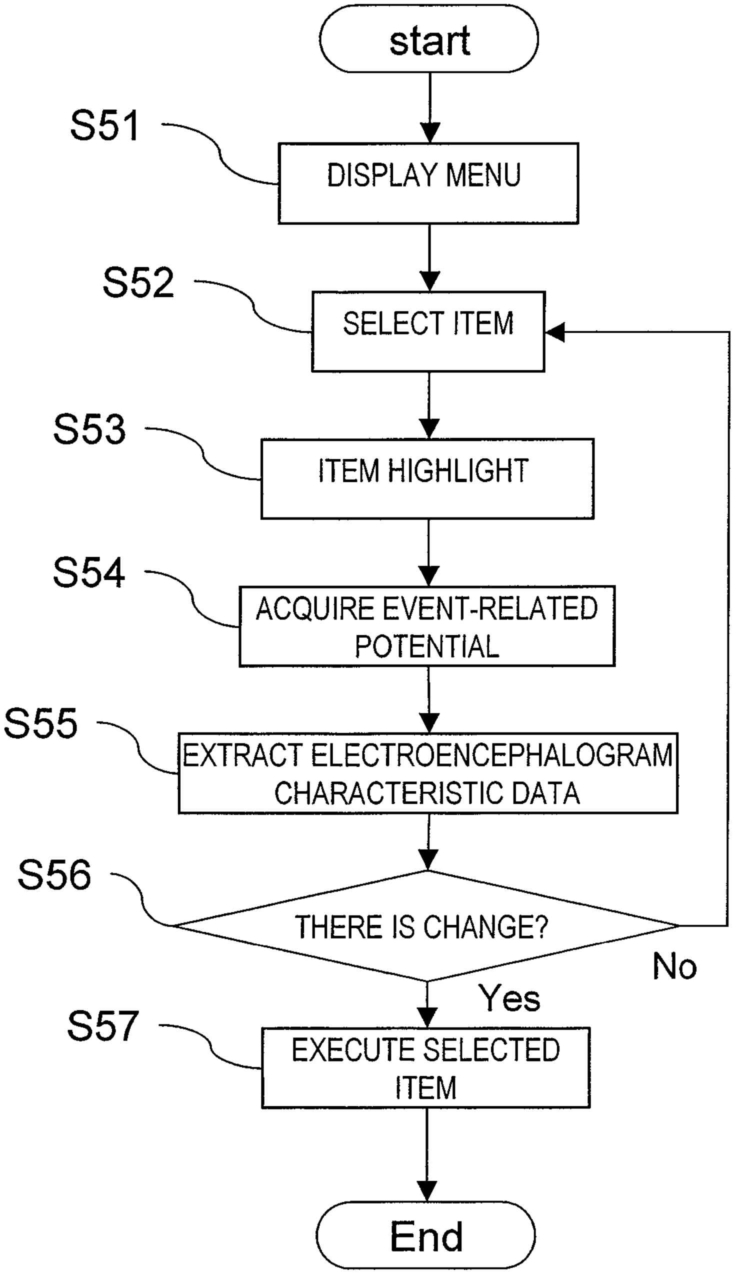
FIG. 10 is a flowchart of processes performed in the electroencephalogram interface system 1.
Figure 11A:
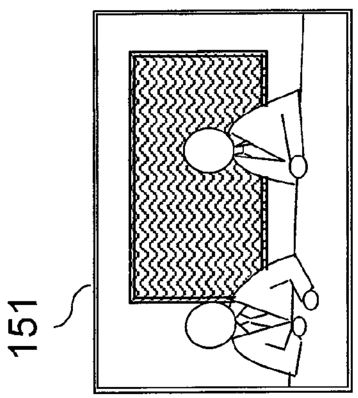
FIG. 11A to 11C are diagrams showing exemplary processes performed in the electroencephalogram interface system 1.
Figure 11B:
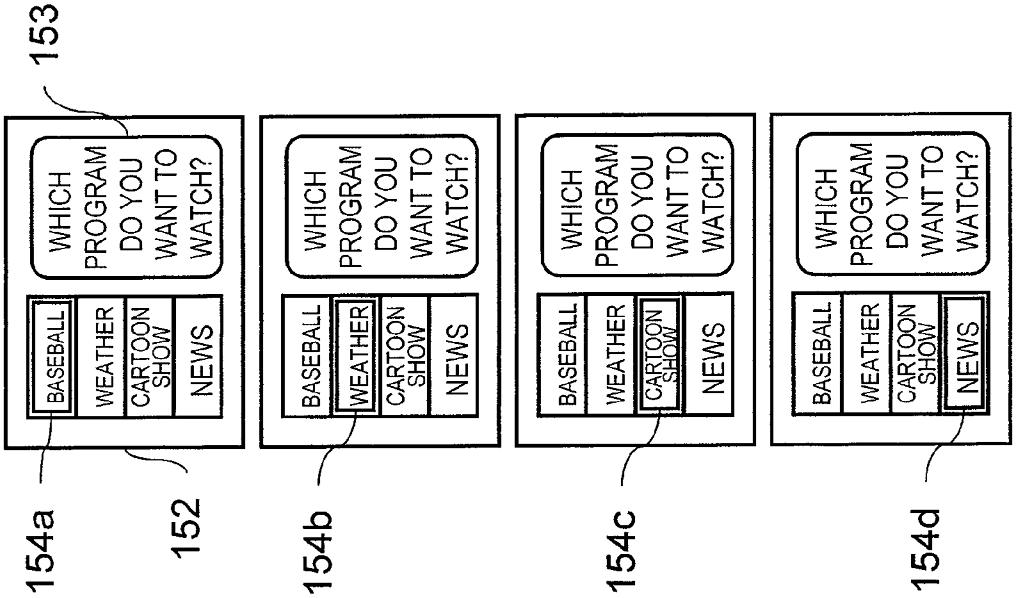
Figure 11C:
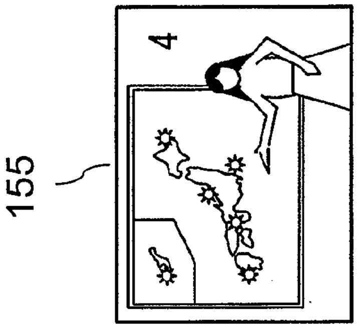

FIG. 10 shows a flowchart of processes performed in the electroencephalogram interface system 1. FIGS. 11A to 11C show exemplary processes to be performed in the electroencephalogram interface system 1. Hereinafter, while referred to FIGS. 11A to 11C as appreciate, an operation of the electroencephalogram interface system 1 of FIG. 10 will be described.

At step S51, the display 16 displays a menu screen. A "menu screen" is a screen on which selection items for causing device manipulations are displayed in the form of a list.

By selecting a desired item from among options in a displayed menu screen, the user 10 is able to perform a device manipulation. Selection of a desired item is realized as the user thinks to himself or herself.

At content viewing, a screen 151 before selection is displayed on the display 16 as shown in FIG. 11A. As the electroencephalogram interface system 1 is activated, a menu item screen 152 as shown in FIG. 11B is displayed. On the screen, a question 153 "Which program do you want to watch?" and options 154 that are candidates of a program whose watching may be desired are presented. Herein, the following four are being displayed: "baseball" 154*a*, "weather forecast" 154*b*, "cartoon show" 154*c*, and "news" 154*d*. Among these four, one is highlight-indicated in a bright color.

At step S52, the electroencephalogram characteristic extraction section 13 determines an item to be highlighted. In the example of FIG. 11B, baseball 154*a* which is at the topmost is determined. Hereinafter, every time step S52 is executed, a next option is consecutively selected for highlighting. After the fourth "news", it returns to the topmost "baseball".

At step S53, the display 16 displays the item determined at step S52 in highlight indication. "Highlight indication" means an indication against a brighter background or in a brighter text color than other items, or an indication pointed to by a cursor or the like. Herein, it suffices if it is clear which item the system currently wants attention to, when looked at by the user 10.

At step S54, the electroencephalogram characteristic extraction section 13 acquires event-related potentials. A plurality of event-related potentials are measured from the potential differences between the ear electrode portion 11 and the respective facial electrode portions 12, which are worn on the face. Stated otherwise, the physical quantities which are measured based on potential differences between the ear electrode portion 11 and the plurality of facial electrode portions 12 worn on the face are the event-related potentials. The moment of highlight indication at step S53 is defined as a starting point of event-related potential acquisition. Each electroencephalogram of 100 milliseconds before to 600 ms after this starting point is acquired, for example. As a result, the response of the user with respect to a highlight-indicated item is acquired. Note that, since the electroencephalogram characteristic extraction section 13 determines the timing of highlighting, it is possible for the electroencephalogram characteristic extraction section 13 to identify a point in time which falls 100 milliseconds before the starting point. Thus, acquisition of event-related potentials can be begun even at a point in time which falls before where the starting point is.

At step S55, the electroencephalogram characteristic extraction section 13 extracts electroencephalogram characteristic data, based on the waveform data of the plurality of measured event-related potentials. The specific method of extracting electroencephalogram characteristic data will be described later.

At step S56, in accordance with the determination criterion stored in the determination criterion DB 15, the determination section 14 distinguishes the extracted electroencephalogram characteristic data.

The distinction is made as to whether the waveform of the currently-acquired electroencephalogram characteristic data is a waveform for an item which the user 10 wishes to select or a waveform for an item that is not wanted to be selected.

At step S57, if the waveform is determined to be that for an item which the user 10 wishes to select, the selected item is executed on the display 16.

The aforementioned determination criterion, a specific example of a distinction method based on the waveform of the acquired electroencephalogram characteristic data, and an exemplary output of the selected item will be described later.

Through the above processing, selection of a menu item is realized based on electroencephalograms, without performing a button manipulation or the like.

Although it is assumed in step S52 that the item to be highlighted is determined in order from top to bottom, a method of random presentation can also be adopted. This may lead to a facilitated determination because, since it is not known in advance which item will be selected, the user 10 will make the selection more carefully, such that the amplitudes of the electroencephalograms will be increased and the characteristic signal to be used for the determination will appear clearly.

Figure 12:
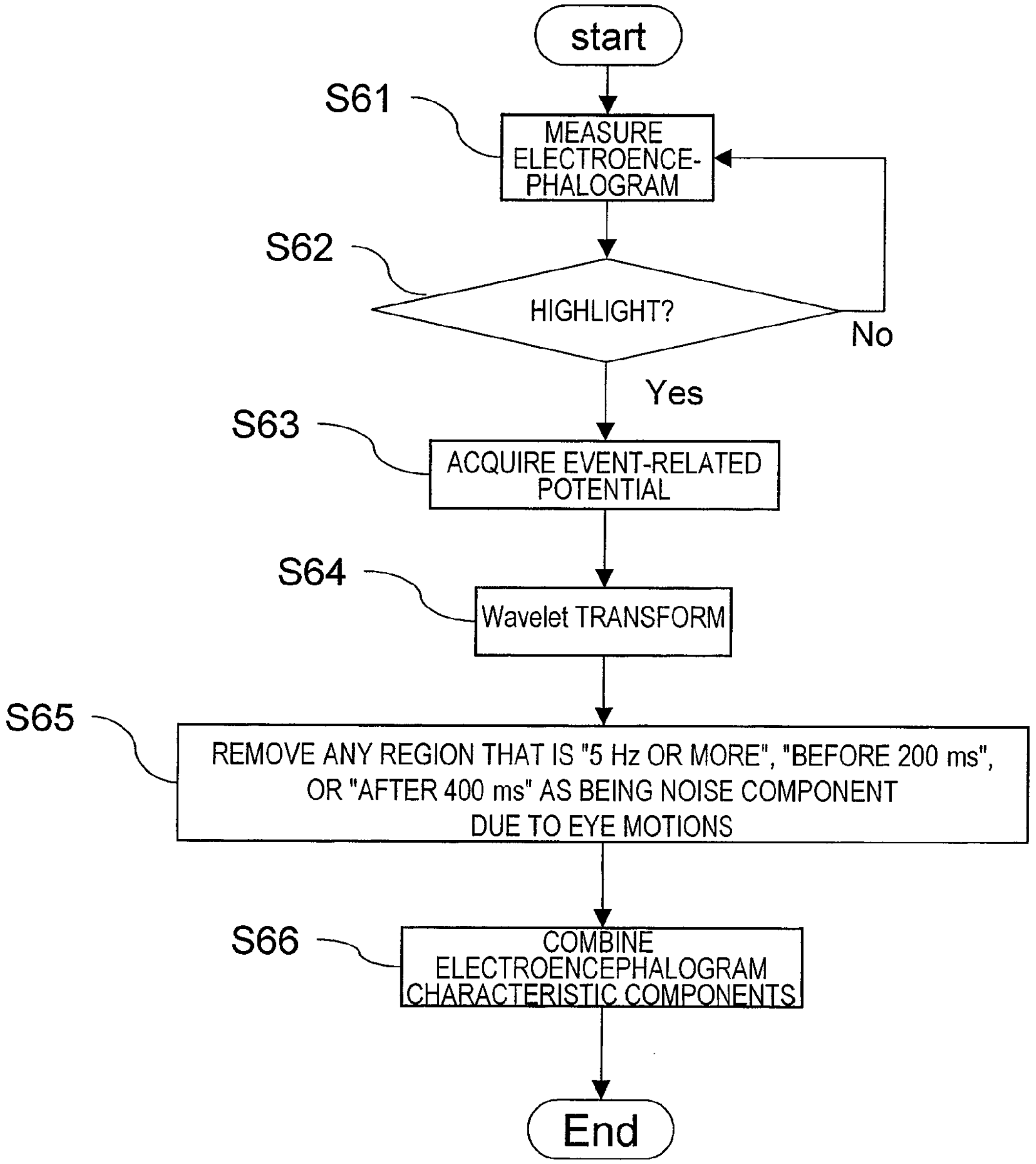
FIG. 12 is a flowchart of processing by an electroencephalogram characteristic extraction section.

Next, the processes of the electroencephalogram characteristic extraction section 13 to be performed at step S51 to step S55 will be described. In the present embodiment, positions of the facial electrode portions that exhibited a high accuracy in the results of the experiment shown in FIG. 6 will be illustrated as an example. It is assumed that the electrode positions of the facial electrode portions 12 are above the left eye 23 (FIG. 2), above the right eye 25 (FIG. 2), and above the right ear 27 (FIG. 2), and that the ear electrode portion 11 is worn at the right mastoid. By using the flowchart of FIG. 12 and the exemplary waveforms of FIG. 13, details of the processes by the electroencephalogram characteristic extraction section 13 will be described.

First, at step S61, on the basis of the ear electrode portion 11, respective potential differences of the plurality of facial electrode portions 12 worn on the face are measured, whereby electroencephalogram measurements are incessantly taken. FIG. 13(*a*) shows examples of electroencephalograms being measured at step S61. Three electroencephalogram waveforms are being simultaneously measured, and the timing of highlighting is also being stored. The three waveforms are as follows.

Waveform 1: electroencephalogram waveform of the electrode above the left eye, on the basis of the right ear electrode portion Waveform 2: electroencephalogram waveform of the electrode above the right eye, on the basis of the right ear electrode portion Waveform 3: electroencephalogram waveform of the electrode above the right ear, on the basis of the right ear electrode portion At step S62, the electroencephalogram characteristic extraction section 13 instructs the display 16 to perform highlighting. On the display 16, item highlights are output as shown in FIG. 11B. The electroencephalogram characteristic extraction section 13 retains the instructed highlight timing, and when highlighting is performed, acquires event-related potentials based on the timing of instructing highlighting as a starting point at step S63.

Specifically, from each of the electroencephalograms of Waveforms 1 to 3 described above, a time section (time width) from −100 milliseconds to 600 milliseconds based on the highlight timing is cut out, thus acquiring three event-related potentials. Moreover, the acquired event-related potentials are subjected to baseline correction. The baseline is the values in a time section from −100 milliseconds to 0 milliseconds. Examples of acquired event-related potentials 1 to 3 are shown in FIG. 13(*b*).

At step S64, the event-related potentials acquired by the electroencephalogram characteristic extraction section 13 are subjected to a time-frequency decomposition (wavelet transform). Through the wavelet transform, each electroencephalogram is itemized into characteristic amounts of time and frequency, thus making it possible to choose and extract an occurrence time slot and a frequency band of a characteristic signal of the electroencephalogram when making a selection. The specific values of the occurrence time slot and the frequency band will be described later. Examples of data obtained by subjecting the event-related potentials of Waveforms 1 to 3 to the wavelet transform are shown in FIG. 13(*c*). The wavelet transform is carried out in a range from 0 to 15 Hz, which includes components of the electroencephalogram, for a time section from 0 ms to 600 ms of each acquired event-related potential. The graphs of FIG. 13(*c*) show data after the wavelet transforms. In the graphs, the horizontal axis represents the time component and the vertical axis represents the frequency component, and portions with thick colors indicate occurrences of an intense power.

At step S65, noise components ascribable to eye motions (saccade) are removed from the wavelet-transformed data, thus cutting out a region that relates to the necessary electroencephalogram characteristic signal. A potential ascribable to minute eye motions (saccade), which would not be measured through parietal measurements, is frequently mixed in an electroencephalogram that is measured on the face. The saccade noise is mainly mixed in a region from 5 to 17 Hz, and presumably, a large amount of noise is also mixed in any electroencephalogram characteristic signal that is contained in this region. Therefore, by cutting out a region which is greater than a frequency of 0 Hz and equal to or less than a frequency of 5 Hz, it becomes possible to extract an electroencephalogram characteristic component which has little noise mixed therein. FIG. 29 shows a region of wavelet-transformed data to be cut out. Region (a) is a collection of data of a frequency region higher than 5 Hz, and should be excluded as a region in which saccade noise has mixed.

Noise influences, e.g., noises mixing due to blinks and responses to visual stimulations, will appear in a time section from after highlighting until 200 ms. Again, although these would not be a problem in parietal measurements, they present a significant problem when electroencephalogram measurements are taken on the face. In order to reduce these noises, a time section from after highlighting until 200 ms and a time section after 400 ms are excluded as noise regions, which are represented as Regions (b) in FIG. 29.

After Regions (a) and (b) are excluded, the remaining region is extracted as data corresponding to an electroencephalogram characteristic component.

The regions to be cut out are shown in FIG. 13(*c*). Each portion surrounded by a dotted line in FIG. 13(*c*) is the region from 200 ms to 400 ms that is at a frequency of 5 Hz or less. With respect to these three Waveforms 1 to 3, sample points contained within the dotted regions are extracted.

At step S66, three electroencephalogram characteristic components from Waveforms 1 to 3 as extracted by the electroencephalogram characteristic extraction section 13 are combined into a single piece of data, which is output as electroencephalogram characteristic data.

Next, a specific example of the determination process by the determination section 14 is described by using a flow diagram of FIG. 14 and a data flow diagram of FIG. 15.

In advance, the determination section 14 stores supervised data representing a waveform with respect to an item that is wanted to be selected and a waveform with respect to an item that is not wanted to be selected.

The "supervised data" is previously acquired and stored through the following procedure. First, a plurality of users (test subjects) are each asked to reveal which option they are going to select in advance, and then select an item in an electroencephalogram interface with electrode positions similar to those employed when actually using an electroencephalogram interface. The event-related potential data recorded at this time are subjected to a wavelet transform as in the above-described electroencephalogram measurement, and sample points in the electroencephalogram characteristic region from 200 ms to 400 ms that is at a frequency of 5 Hz or less are extracted. The sample points in the electroencephalogram characteristic region extracted from a plurality of electrode combinations are combined into a single piece of data, thus generating electroencephalogram characteristic data. The electroencephalogram characteristic data is classified into those pertaining to an item that is wanted to be selected and those pertaining to an item not wanted to be selected (unselected), and is stored as supervised data in which electroencephalogram characteristic data is associated with the aforementioned classifications.

This supervised data may be generated based on electroencephalograms of an indefinite number of people as described above. Alternatively, the user 10 who uses the electroencephalogram interface may perform a learning task in a similar manner in advance, and supervised data may be generated by utilizing the electroencephalogram of that user 10.

At step S81, the determination section 14 acquires the electroencephalogram characteristic data for each item from the electroencephalogram characteristic extraction section 13. To explain based on the example of FIGS. 11A to 11C, from the electroencephalogram characteristic extraction section 13, the determination section 14 receives electroencephalogram characteristic data (41*a*, 41*b*, 41*c*, 41*d*) based on starting points which are the points of highlighting the four items "baseball", "weather forecast", "cartoon show", and "news" in the electroencephalogram interface as shown in FIG. 15.

At step S82, the determination section 14 calculates a similarity level which represents how much a piece of electroencephalogram characteristic data resembles a waveform with respect to an item that is wanted to be selected. The determination section 14 stores supervised data in advance as described above, and the similarity level calculation utilizes the waveforms with respect to an item that is wanted to be selected and the waveforms with respect to an item that is not wanted to be selected, which are contained in the supervised data. The waveforms contained in the supervised data are classified into the two groups of waveforms (correct waveform) with respect to an item that is wanted to be selected and waveforms (incorrect waveform) with respect to an item that is not wanted to be selected, and the distances between the measured electroencephalogram characteristic data and the correct waveform group and the incorrect waveform group are calculated, thus calculating a similarity level with the correct waveform group. The similarity level calculation utilizes a linear discriminant technique. A posterior probability that the measured electroencephalogram characteristic data belongs to the correct waveform group is utilized.

Similarly, the determination section 14 calculates a similarity level for the electroencephalogram characteristic data with respect to each item. For example, as shown in FIG. 15(*b*), similarity levels (posterior probabilities) are calculated respectively for Items 1 to 4.

In the present embodiment, a linear discriminant technique is employed in the similarity level calculation. Alternatively, a technique such as a support vector machine or a neural network may be employed, where a similarity level with a correct waveform group is calculated by calculating how close to the correct waveform group the measured electroencephalogram characteristic data is, from a border line between the correct waveform group and the incorrect waveform group (i.e., the distance from the border line).

At step S83, the determination section 14 compares the similarity level values of the electroencephalogram characteristic data which have been calculated for the respective items, chooses a waveform that most resembles the correct waveform, and outputs this waveform as the comparison result. For example, the determination section 14 distinguishes the item whose similarity level value is the largest as the item selected by the user 10. In the example of FIG. 15, the respective similarity levels are 0.76, 0.30, 0.22, and 0.28, among which "Item 1" having the largest similarity level is distinguished as the selected item, thus producing a result as shown in FIG. 15(*c*). The result of distinction is output on the display 16 by the determination section 14.

Next, an exemplary output of the display 16 will be described. In an exemplary interface where a genre of a video content is to be selected as shown in FIG. 11B, if a waveform is determined as pertaining to an item which the user 10 wishes to select, a video that matches the selected item is output through a video outputting device. For example, if "weather forecast" is selected in the item selection example illustrated in FIG. 11B, a video 155 of a weather forecast is output as shown in FIG. 11C.

Although the present embodiment describes the display 16 as a specific example of the output section 16 of FIG. 7, the specific construction of the output section may be adapted to the output to be controlled. For example, in the case where an audio output (e.g., music reproduction) is to be made instead of or in addition to a video output (e.g., content displaying in accordance with the selected item), the output section 16 may include a driving control circuit for loudspeakers. Furthermore, in the case where an external device such as an amplifier or an audio player is to be manipulated, a control circuit for outputting a control signal to the external device, an output terminal, and the like are encompassed by the output section 16. In the case where a vibration output is to be made (where a response is notified to the user via vibration), the output section may include a driving control circuit for a vibrator.

The present embodiment illustrates an exemplary electroencephalogram interface which, based on a selected item, outputs a video that matches the item. However, the present invention also encompasses any electroencephalogram interface which merely outputs a result of determination on the screen, or which does not even output a result of determination.

Through the above processing, by using electrodes which are disposed at an ear periphery and on the face, an item selected by the user can be determined with an accuracy similar to that obtained in the case where an electrode is disposed at the parietal. This makes it unnecessary for the user to wear any electrodes other than a wearable device such as an HMD, and reduces the burden associated with device wearing because electrode attachment is accomplished at the same time the wearable device is worn.

Next, the details and results of an experiment performed by the inventors will be described, and particulars of the present embodiment and the effects thereof will be described.

FIG. 16 shows examples of positions which are in contact with the face of a user 10 in this experiment, where the HMD-type electroencephalogram interface system 1 is employed. Electrodes are disposed so as to be in contact with these positions. A specific study of accuracy was conducted by using electrodes at these positions.

First, the inventors performed a measurement experiment for 15 test subjects in their twenties, among whom test subjects that maintained a high arousal level were subjected to analysis. The test subjects were the same as the test subjects in the aforementioned evaluation experiment.

As for the electroencephalogram measurement, Polymate AP-1124 (manufactured by DIGITEX LAB. CO., LTD) was used, with a sampling frequency of 200 Hz and a time constant of 3 seconds, and with a 30 Hz low-pass filter being used for filtering.

The electrodes were disposed in 4 places. The ear electrode portion 11 was at the right mastoid 31 (FIG. 16), which was defined as the reference electrode. The facial electrode portions 12 were disposed at: "above the left eye" 23 (FIG. 16), which was 4 cm above the central portion of the left eye; "above the right eye" 25 (FIG. 16), which was 4 cm above the central portion of the right eye; and "above the ear" (above the right ear) 27 (FIG. 16), which was 2 cm above the uppermost portion of the root of the right ear. A ground electrode was worn at FPz33 (FIG. 16) according to the position notation of the International 10-20 system. Moreover, for a comparison with electroencephalogram measurements at the parietal, an electrode was also worn at Pz according to the position notation of the International 10-20 system.

Each test subject was asked to make 40 selections. Irrespective of whether the measurements were taken on the front part of the face or taken at Pz, determinations were made by using the same determination algorithm. The rate at which the results of determination proved correct was calculated as the distinction ratio, thus performing an accuracy check.

In the determination algorithm subjected to evaluation, wavelet data was generated by performing the processes from step S63 to step S64 above, and a determination process was performed for electroencephalogram characteristic components which have been subjected to the process of removing noises (e.g., electro-oculographic potential) at step S65.

Specifically, data of an event-related potential from 0 ms to 600 ms based on the highlight timing as a starting point (sampling interval: 5 ms; double-type) was subjected to a wavelet transform. In the wavelet transform, the number of samples for the frequency component was 40 samples at 15 Hz or less, and the number of samples for the time component was 140 samples between 0 ms and 600 ms, thus realizing a transform into 40×140 wavelet data. Furthermore, in order to smooth out the noises in the wavelet data, the wavelet data was subjected to a 4×20 resampling (a double-type where the frequencies from 0 to 15 Hz were divided into four, and the time from 0 to 600 ms was divided into twenty), thus calculating wavelet-transformed data of the event-related potential.

Each electroencephalogram characteristic component at step S65 (a region from 200 ms to 400 ms that was at 5 Hz or less) was obtained by extracting the time-frequency domain shown in FIG. 13(*e*) from the wavelet-transformed data of the aforementioned event-related potential. Specifically, a total of 12 samples, i.e., a frequency component in a region spanning two components of lower frequencies among the 4-divided components and a time component in a region between 210 ms and 390 ms (a region spanning the $8^{th}$ to $13^{th}$ samples), were extracted as an electroencephalogram characteristic region. The data of electroencephalogram characteristic regions extracted for the respective electrode combinations were combined into a single piece of data, thus becoming electroencephalogram characteristic data. In this experiment, electroencephalogram characteristic components were extracted from the three electroencephalograms of: a combination of "above the left eye" and "on the basis of an ear"; a combination of "above the right eye" and "on the basis of an ear"; and a combination of "above the right ear" and "on the basis of an ear". Therefore, electroencephalogram characteristic data having 36 sample points, obtained by combining three sets of 12 sample points, was generated.

Through a linear discrimination of the electroencephalogram characteristic data of 36 sample points generated through the above-described processes, the determination section 14 makes a determination as to whether a waveform pertains to an item that is wanted to be selected.

Now, a data structure and a method of generating the supervised data to be used for the determination process by the determination section 14 are described.

FIG. 17 shows an example of supervised data. This supervised data is generated in advance, and stored in the determination criterion DB 15. The method of generating the supervised data is as follows.

First, the same user 10 is asked to reveal which option he or she is going to select in advance, and then select an item in an electroencephalogram interface with similar electrode positions. The event-related potential data recorded at this time is subjected to a wavelet transform as in the above-described electroencephalogram measurement, and from each electrode combination among the positions shown in FIG. 16, 12 sample points in the electroencephalogram characteristic region from 200 ms to 400 ms that is at a frequency of 5 Hz or less are extracted. The sample points in the electroencephalogram characteristic region extracted from the three electrode combinations are combined into a single piece of data, thus generating electroencephalogram characteristic data of 36 sample points. Furthermore, in order to classify each piece of electroencephalogram characteristic data into data pertaining to an item that is wanted to be selected or data pertaining to an item not wanted to be selected (unselected), correct-incorrect indices are assigned to the electroencephalogram characteristic data; specifically, "+1" is assigned to any electroencephalogram characteristic data pertaining to an item that is wanted to be selected and "−1" is assigned to any electroencephalogram characteristic data pertaining to an item which is not wanted to be selected. The result of this is retained as supervised data.

The determination section 14 performed a similarity level calculation between the plurality of pieces of electroencephalogram characteristic data in the supervised data and the 36 sample points of electroencephalogram characteristic data currently measured from the user 10. With a linear discrimination approach, a probability (posterior probability) that the electroencephalogram characteristic data currently measured from the user 10 was included in the "+1" group in the supervised data as shown in FIG. 17 was calculated, thus calculating a similarity level. Similarly, a similarity level was calculated for the electroencephalogram characteristic data measured with respect to each item. The determination section 14 made a comparison between the similarity levels calculated for the respective items, and determined that the item having the largest value corresponded to an item that was wanted to be selected, in the electroencephalogram currently measured from the user 10.

The results of the accuracy checks are shown in FIG. 18.

From the results of the experiment, the accuracy of an electroencephalogram interface utilizing electroencephalogram measurement of a potential difference of an electrode worn on the face on the basis of a mastoid was, as shown in FIG. 6, (1) 75.0% when utilizing an electroencephalogram of the electrode above the left eye based on a reference electrode at the right mastoid, (2) 75.3% when utilizing an electroencephalogram of the electrode above the right eye based on a reference electrode at the right mastoid, and (3) 68.1% when utilizing an electroencephalogram of an electrode above the right ear based on a reference electrode at the right mastoid.

When a determination was made by utilizing the present invention, with electroencephalogram characteristic regions extracted from the electroencephalograms of Waveforms 1 to 3 and combined into electroencephalogram characteristic data, the accuracy was 80.6%, indicative of improvements of 10% or more (at the most) over the distinction ratios individually obtained with Waveforms 1 to 3 before combining electrodes. The distinction ratio of about 80% is approximately equivalent to the accuracy of the case where Pz is employed for measurement.

Now, by redefining the electroencephalogram characteristic component of Waveform 1 to be a region from 200 ms to 400 ms that is at 15 Hz or less, for example, the number of data was doubled to 24 samples, and a distinction ratio was calculated by performing a distinction by utilizing the electroencephalogram characteristic component of Waveform 1. The resultant distinction ratio was 72.5%, which represents little improvement in accuracy over the accuracy of the case where 12 samples were used, i.e., 75.0%.

This indicates that accuracy improvements cannot be obtained by merely increasing the number of samples used for distinction. If any sample points containing noise exist among the sample points used for distinction, the possibility of noise mixing increases regardless of whether it is an item which the user 10 wishes to select or not, thus resulting in a deteriorated distinction ratio due to an increased likelihood for the noise to distinguished as a characteristic signal of the electroencephalogram. In other words, it is considered more vital to the distinction accuracy whether the sample points contain much noise or not than how many sample points there are to be used for distinction.

Thus, it is considered that accuracy improvements cannot be attained by increasing the number of samples of an electroencephalogram characteristic component through mere combinations or the like, but can only be attained by utilizing electroencephalogram characteristic data which is obtained by combining characteristic components after removing the noise components due to eye movements therefrom.

The above experimental results indicate that, by extracting characteristic data from the potentials of a plurality of facial electrodes on the basis of an ear periphery (mastoid), and subjecting the combined data to determination, a more accurate electroencephalogram interface can be constructed than in the case where determination is made with a electroencephalogram that is measured with an ear electrode portion and a facial electrode alone.

It can also be seen that, with the improved accuracy according to the present invention, an electroencephalogram interface can be constructed with an accuracy similar to the case where an electroencephalogram is measured at the parietal.

Thus, through wavelet transforms of event-related potentials which are measured on the face on the basis of an electrode in an ear periphery, characteristic signal components are extracted, from which noises due to eye motions are removed, and characteristic signal components from the plurality of electrodes are combined to generate electroencephalogram characteristic data which is utilized for determination. This makes it possible to make a determination with a high accuracy similar to the case of wearing an electrode at the parietal, and eliminates the need to wear any electrodes other than a wearable device such as an HMD, whereby the user's burden of device wearing can be reduced.

The above-illustrated example (FIG. 11A to 11C) is directed to a case of controlling displayed substance on the display 16. However, controlling of a displayed substance is only an example. Hereinafter, with reference to FIG. 19 and FIG. 20, an example of controlling an external device will be described.

FIG. 19 shows an electroencephalogram interface system 1*a* according to a first variant of the present embodiment. A transmission device 4 is provided on an eyeglasses-type head-mount display (HMD) 100*a* in the electroencephalogram interface system 1*a*. Otherwise, the construction is similar to the construction shown in FIG. 8.

The displayed substance on a display 16 of the HMD 100*a* is controlled based on measured event-related potentials of the user, and the operation of an air conditioner 3 is controlled. For example, an operation menu (e.g., "cool", "warm", "dry") of the air conditioner 3 is displayed on the display 16, and is highlighted in order. When a desired item is highlighted, the user thinks that he or she wants to select that item. Then, through the aforementioned processing, the item wanted to be selected is identified based on his or her event-related potentials. The determination section 14 generates a control signal corresponding to that item, which is output via the transmission device 4.

A reception device 5 of the air conditioner 3 receives the control signal transmitted from the transmission device 4. As a result, the air conditioner 3 begins an operation corresponding that control signal.

Note that the transmission device 4 and the reception device 5 are an infrared transmitter and an infrared receiver, for example.

FIG. 20 shows an electroencephalogram interface system 1*b* according to a second variant of the present embodiment. An eyeglasses-type controller 100*b* in the electroencephalogram interface system 1*b* has a transmission device 4 provided thereon, but no display. Instead of the display of the earlier variant, the electroencephalogram interface system 1*b* includes a TV 7 as a device to be controlled. A communication device 6*a* which is provided on the eyeglasses-type controller 100*b* is capable of bi-directional communications with a communication device 6*b* provided on the TV 7. The substance to be displayed on the display 16 of the TV 7 is as described above. The eyeglasses-type controller 100*b* functions as a control device for controlling the displayed substance on the TV 7.

As is clear from this variant, the output section 16 in FIG. 7 may be a display which is provided within the same housing as that of the determination section 14 and the like, or may be a display which is provided in a different housing.

Although the present embodiment illustrates an example where the reference electrode is on a mastoid, it is not a limitation that an ear electrode portion be worn at a mastoid. In conventional electroencephalogram measurements, too, mastoids and earlobes are similarly often utilized as sites that are immune to the influences of an electroencephalographic potential, an electrocardiographic potential, and a myoelectric potential. Therefore, any case of wearing an ear electrode portion in an ear periphery, including an earlobe, a tragus, and an ear root rear portion as shown in FIG. 4B, is encompassed within the scope of the present invention.

The above description of processing is directed to an HMD for example. However, the scope of the present embodiment extends to any electroencephalogram interface employing an ear electrode worn in an ear periphery and a plurality of facial electrode portions worn on the face, and the apparatus to be realized is not limited to an HMD. FIG. 21 shows an example of a therapy bed for massaging, as an example other than HMDs.

The user lies on a therapy bed for massage with his or her face down, and receives a massage therapy while having the face fixed in a hole which opens in the bed. At this portion for fixing the face, electrodes are disposed so as to be in contact with an ear periphery and the face of the user, and a television set (not shown), for example, is provided at the bottom of the hole for displaying a menu. This television set is provided to allow the user to view a broadcast program during the massage therapy. As menu items constituting a part of the menu, functions of a device for manipulation are displayed. When a desired menu item becomes highlighted, as the user thinks to themselves that he or she wants to use that function, e.g., channel switching, the channel is switched during the therapy. Thus, device control via an electroencephalogram interface system is realized.

Thus, the present invention is applicable to an interface of any goggles-type device other than an HMD, or an interface of any device where the face is to be fixed in a specific place, e.g., a therapy bed.

The present embodiment illustrates that supervised data which is generated from the electroencephalogram characteristic data of an indefinite number of users is stored in the determination criterion DB 15 as a determination criterion and utilized for linear discrimination. Alternatively, the determination criterion may be a threshold value, and determination of an electroencephalogram waveform with respect to an item that is wanted to be selected may be made based on whether any value that is greater than this threshold value is contained in the extracted electroencephalogram characteristic data of the user 10. In that case, a threshold value is retained in the determination criterion DB.

Embodiment 2

In Embodiment 1, determination is made by extracting electroencephalogram characteristic data from electroencephalograms obtained by using a reference electrode in an ear periphery and a plurality of electrodes at facial positions.

In the case of a device which cannot be stably worn, e.g., an HMD, it may often happen that the electrodes worn on the face become dislocated or detached, or that the reference electrode worn in an ear periphery become dislocated or detached. Moreover, it may often happen that contact between the electrodes and the skin become poor due to the skin state, which is susceptible to perspiration, the outside air temperature, and characteristics of each individual person such as dry skin, thus causing the electrodes to come off the skin. It may also often happen that impurities, e.g., sweat, come between the electrodes and the skin to cause an increased noise, such that electroencephalogram signals can no longer be correctly measured.

Thus, the present embodiment illustrates an electroencephalogram interface system in which the invention of Embodiment 1 still applies even if an insufficiency in the state of attachment occurs in one of the electrodes, thus performing an electroencephalogram determination with a stable accuracy.

FIG. 22 shows a construction diagram of an electroencephalogram interface system 2 according to the present embodiment. Constituent elements which are identical to those of Embodiment 1 will be denoted by like reference numerals, and the descriptions thereof will be omitted.

The electroencephalogram interface system 2 of the present embodiment differs from the electroencephalogram interface system 1 of Embodiment 1 in that there is a plurality of ear electrode portions 11, and that an electrode attachment determination section 17 is newly introduced. The electrode attachment determination section 17 determines whether each electrode that is worn is properly worn. Among the main constituent elements, only the electrode attachment determination section 17 differs; however, the internal processing of the electroencephalogram characteristic extraction section 13 receiving a signal from the electrode attachment determination section 17 is also different.

The flowchart of the overall processing of the present embodiment is identical to the flowchart of FIG. 10 according to Embodiment 1. Therefore, a flowchart concerning the electroencephalogram characteristic data extraction process in the electroencephalogram characteristic extraction section 13 will be described, and the electrode attachment determination section 17 and the specific processes will be described.

FIG. 23 shows a flowchart of an electroencephalogram characteristic data extraction process in the electroencephalogram characteristic extraction section 13. The description will be simplified with respect to any step where the same process as in Embodiment 1 is performed. The details of each step will be specifically described later.

At step S101, the electrode attachment determination section 17 determines a state of attachment of each electrode (the ear electrode portions 11 and the facial electrode portions 12) worn by the user 10, and outputs electrode attachment information. As used herein, a "state of attachment" means whether or not an electrode has been, or is becoming, detached from the skin, and so on. The determination is made by examining electrical characteristics between electrodes. Specifically, the determination is made by checking the impedance between electrodes.

At step S102, based on the electrode state information that has been determined by the electrode attachment determination section 17, the electroencephalogram characteristic extraction section 13 selects a combination of electrodes to be measured.

At step S61, the electroencephalogram characteristic extraction section 13 measures a potential difference in the selected electrode combination, thus measuring an electroencephalogram.

At step S62, with an instruction from the electroencephalogram characteristic extraction section 13, a highlight indication is performed by the output section 16.

A step S63, with respect to the electroencephalogram measured for each selected electrode combination, the electroencephalogram characteristic extraction section 13 acquires an event-related potential based on the timing of instructing highlighting as a starting point.

At step S64, a wavelet transform is performed in order to itemize each acquired event-related potential into characteristic amounts of time and frequency.

At step S65, only a region concerning each electroencephalogram characteristic signal is cut out from the wavelet-transformed data.

At step S66, the plurality of electroencephalogram characteristic components which have been cut out by the electroencephalogram characteristic extraction section are combined into a single piece of data, and output as electroencephalogram characteristic data.

The subsequent determination process to be performed by the determination section 14 and the exemplary output of the output section 16 are identical to those described in Embodiment 1.

Next, with reference to FIG. 24, a method for determining a state of electrode attachment in the electrode attachment determination section 17 will be described. It is assumed that the electrodes are worn at positions 11*a*, 11*b*, 12*a*, and 12*b* shown in FIG. 24. Specifically, the user 10 is wearing an ear electrode portion 11*a* in the right ear periphery, an ear electrode portion 11*b* in the left ear periphery, a facial electrode portion 12*a* above the right ear, and a facial electrode portion 12*b* above the left eye.

FIG. 25 shows a flowchart of the processing by the electrode attachment determination section 17.

At step S71, the electrode attachment determination section 17 determines insufficiencies of wearing between electrodes via impedance check. As a result, it can be determined whether the electrodes are in contact with the user's skin.

As used herein, an impedance check is an approach of flowing a very minute amount of current between two electrodes to measure a value of resistance existing between the places where the two electrodes are in contact with the skin. If an electrode(s) becomes detached or perspiration of the user or the like prevents proper detection of electroencephalograms, there is an increase in the resistance value between the electrodes. Therefore, by performing impedance checks to measure resistance values between electrodes, it becomes possible to determine which combination of electrodes fails to attain proper contact.

Electrode combinations of electrodes 12*a* and 12*b* worn on the face, against both ear electrode portions 11*a* and 11*b* shown in FIG. 24, are: a combination 201 of the ear electrode portion 11*a* and the facial electrode portion 12*a*; a combination 202 of the ear electrode portion 11*b* and the facial electrode portion 12*a*; a combination 203 of the ear electrode portion 11*a* and the facial electrode portion 12*b*; and a combination 204 of the ear electrode portion 11*b* and the facial electrode portion 12*b*. The electrode attachment determination section 17 performs impedance checks in the four electrode combinations 201, 202, 203, and 204 to measure resistance values in the respective combinations.

At step S72, the electrode attachment determination section 17 determines whether, among the resistance values of the electrode combinations 201, 202, 203, and 204, any plural number of resistance values exist that are higher than the others or not. Specifically, if the resistance value of a given combination of electrodes measured at step S72 exceeds 100 kΩ (kiloohms), it is determined that either electrode in that electrode combination has insufficient contact.

If there is no electrode combination that has a higher resistance value than others, electrode state information that "there is no insufficient electrode" is output to the electroencephalogram characteristic extraction section 13 at step S74.

For example, if a resistance value is about 5 kiloohms, that pair of electrodes can be considered to be both worn well.

It has been illustrated that the check of step S71 for insufficiencies of wearing among electrodes and the check of step S72 for combinations which are insufficiently worn are made via impedance checks. Alternatively, an electroencephalogram may be measured for each electrode combination, and characteristics of the electroencephalograms, e.g., frequency, may be utilized for detecting insufficiencies of wearing among electrodes. For example, by checking the number of times that a measured electroencephalogram has exceeded ±100 μV or checking the frequency components of a measured electroencephalogram, it is possible to determine a state of electrode attachment. In the case where an electrode state is determined by utilizing waveform characteristics rather than a resistance value as described above, the check of step S72 is made as to whether any plural number of electrode combinations exist which exhibited electroencephalograms with characteristics indicative of insufficiencies of electrode wearing.

If step S72 finds that a plurality of electrode combinations that have insufficiencies of wearing exist, at step S73, the electrode attachment determination section 17 identifies an insufficient electrode by searching for an electrode which is commonly included among electrode combinations having insufficiencies of wearing. Generally speaking, in a detection of insufficiencies of wearing based on impedance checks or waveform characteristics, it is only possible to determine one of a given electrode combination has an insufficiency. Therefore, by detecting a plurality of electrode combinations having insufficiencies of wearing, and identifying an electrode that is commonly included among the plurality of combinations, it becomes possible to identify an insufficiency as to which electrode is actually detached, and so on. For example, if the resistance value of the electrode pair 201 and the resistance value of the electrode pair 202 in FIG. 24 are large, the facial electrode portion 12*a* which is common to both combinations is identified as an electrode which is insufficiently worn.

After identifying an electrode which is insufficient, at step S74, the electrode attachment determination section 17 outputs position information of the identified electrode to the electroencephalogram characteristic extraction section 13 as electrode state information. If the facial electrode portion 12*a* is insufficiently worn, for example, information that the "electrode above the right ear is insufficient" is output as the electrode state information.

Although the above example illustrates a case where determination of a state of electrode attachment is made via impedance checks or electroencephalogram measurements, additional sensors such as pressure sensors may be introduced to the electrodes to determine the state of attachment of each electrode based on the intensity of contacting pressure.

Although the electrode state information is illustrated above to be either "there is no insufficient electrode" or "electrode above the right ear is insufficient", for example, the electrode attachment determination section may notify absence of insufficient electrodes by not making any output. In the case where each electrode has a unique ID, an electrode ID may be output to notify the presence of an insufficient electrode.

Furthermore, if the resistance value of an electrode combination does not exceed 100 kiloohms but is close to 100 kiloohms (e.g., in the range from 80 to 100 kiloohms), it is presumable that an electrode(s) is becoming detached. The electroencephalogram signal which is obtained by using any such electrode has a low reliability, and if it is used for subsequent processing, the determination accuracy of the electroencephalogram interface system 2 may possibly be deteriorated. Therefore, an electrode which is becoming detached may be identified through the same method as that for a complete electrode detachment described above, and the event-related potential obtained from that electrode may be discarded, or a notification of the insufficient electrode may be made. Moreover, the event-related potential obtained from any such electrode may be subjected to processing, e.g., noise removal.

Next, the processing by the electroencephalogram characteristic extraction section 13 will be described with respect to exemplary measurements in the respective states of electrode attachment shown in FIGS. 26(*a*) to (*c*).

The electroencephalogram characteristic extraction section 13 receives electrode state information from the electrode attachment determination section 17, and determines a combination of electrodes with which to perform an electroencephalogram measurement.

When electrode state information that "there is no insufficient electrode" is received from the electrode attachment determination section 17, as shown in FIG. 2A, the electroencephalogram characteristic extraction section 13 measures electroencephalograms from potential differences of a plurality of facial electrode combinations (electrode pairs 201, 202, 203, and 204 in FIG. 24) on the basis of both ear electrode portions 11*a* and 11*b*.

When electrode state information that the "electrode above the right ear is insufficient" is received from the electrode attachment determination section 17, as shown in FIG. 26B, the electroencephalogram characteristic extraction section 13 measures electroencephalograms from potential differences of the electrode combinations 203 and 204 (which do not involve the electrode above the right ear 12*a*) on the basis of the ear electrode portions 11*a* and 11*b*.

When electrode state information that the "right ear electrode portion is insufficient" is received from the electrode attachment determination section 17, as shown in FIG. 26C, the electroencephalogram characteristic extraction section 13 measures electroencephalograms from potential differences of the facial electrode combinations 202 and 204 (which do not involve the ear electrode portion 11*a*) on the basis of the left ear electrode portion 11*b*.

Thus, by incessantly monitoring the states of electrode attachment and performing a determination by combining electrodes excluding any insufficiently-worn electrodes, even if the electrodes on the face or in an ear periphery are detached, a plural number of facial electrodes can be used for measurements on the basis of the ear electrode portions 11, whereby a highly accurate determination can be maintained. Moreover, even if an ear electrode portion 11 is detached, the operation of the electroencephalogram interface can be continued.

Moreover, since insufficiently-worn electrodes are identified, it is possible to present a message for asking that a specific electrode be positioned back in place, e.g., "Make sure that the electrode behind the right ear is worn correctly", or notify the user 10 with an alarm sound that an insufficient electrode attachment has occurred. Such messages permit the user 10 a simple cure of pressing the site of any electrode that is insufficiently worn, for example, rather than having to go through the motion of wearing the HMD again (which would require even the normally-worn electrodes to be positioned back in place), and thus reduce the user's burden of electrode wearing. Furthermore, the ease of coping with insufficiencies of electrode wearing makes it possible to constantly maintain normal states of electrode wearing, whereby a circumstance which enables highly accurate determinations is sustained.

Moreover, in a case where the user 10 does not receive any notification of insufficiencies of wearing even when an insufficiency of electrode wearing occurs, the HMD may have a mechanism for improving the state of electrode attachment (e.g., an adjustment for changing the endpiece portion shapes of the HMD so that the HMD is in tighter contact with the user 10, or an adjustment for causing a specific electrode of the HMD to be strongly pressed against the user 10 by utilizing a spring or air pressure), thus making it possible to automatically maintain a normal state of electrode attachment, and sustain a circumstance which enables highly accurate determinations without bothering the hands of the user 10.

Therefore, even if an HMD is worn unstablely, an electroencephalogram interface can be operated in a robust manner.

Next, the details and results of an experiment performed by the inventors will be described, and the effects of the present embodiment will be described.

In the experiment, the operation accuracy of an electroencephalogram interface system according to the present embodiment which works on the basis of both mastoids was examined, where electrode detachments were contemplated. Also, the accuracy of an approach which works on the basis of one mastoid was compared, where electrode detachments occurring at similar positions were contemplated.

As for the experimental parameters, an electroencephalograph and a filtering process similar to those in the experiment performed in Embodiment 1 were performed, and also a similar method of accuracy calculation was adopted.

The positions of the electrodes for measurement were the following 4 places in total. As ear electrode portions, reference electrodes were placed at a right mastoid 11*a* (FIG. 24) and a left mastoid 11*b* (FIG. 24). As facial electrode portions, electrodes were worn "above the left eye" 12*b* (FIG. 24), which was 4 cm above the central portion of the left eye, and "above the ear" (above the right ear) 12*b* (FIG. 24), which was 2 cm above the uppermost portion of the root of the right ear. A ground electrode was worn at FPz according to the position notation of the International 10-20 system. The approach which works on the basis of only one ear mastoid was carried out at the positions shown in FIG. 16, similarly to the electrode positions described in Embodiment 1.

The results of the accuracy checks are shown in FIG. 27.

The experimental results indicated that, in the approach of the present embodiment, the distinction ratios in the three cases of (a) when normal as shown in FIG. 26A, (b) when the facial electrode portion 12*a* was detached as shown in FIG. 26B, and (c) when the ear electrode portion 11*a* was detached as shown in FIG. 26C, were, respectively, (a) 80.6%, (b) 75.6%, and (c) 69.1%. Thus, it was confirmed that the present embodiment ensures that a distinction ratio of almost 70% is maintained even if one electrode is detached, thus enabling operation of the electroencephalogram interface.

Moreover, a comparison was made between the approach of the present embodiment and the case which works on the basis of one mastoid. On the basis of one mastoid, the distinction ratio was 75.0% for case (b), which is lower than that of the present embodiment utilizing both mastoids, and the electroencephalogram measurement was impossible in case (c), i.e., the electroencephalogram interface could not be operated.

The above experimental results indicate that, by extracting characteristic data from the potentials of a plurality of electrodes on the face on the basis of both mastoids, and subjecting combined data to determination, a higher accuracy is obtained than in the case where determination is made based solely on the potential differences between one mastoid and portions on the face, and that an electroencephalogram interface can be operated with a relatively high accuracy even if one electrode is detached, without making the measurement impossible.

Thus, with an electroencephalogram interface according to the present embodiment, one electrode is worn at each ear periphery and a plurality of electrodes are worn at facial positions, such that, even when one electrode is detached, potentials of a plurality of facial electrodes are still obtained on the basis of a reference electrode in an ear periphery. Thus, deteriorations in the determination accuracy and inability to make determinations due to insufficiencies of electrode wearing can be avoided, thus making it possible to realize a robust electroencephalogram interface even if a device such as an HMD is worn unstably.

An electroencephalogram interface apparatus according to the present invention is broadly applicable to the case where electroencephalogram measurements are to be taken on the face. An electroencephalogram interface apparatus according to the present invention can be used not only in conjunction with an HMD, but also when constructing an interface utilizing an electroencephalogram in an eyeglasses (goggles)-type wearable device which does not provide any video output, a device in which the face is fixed at a specific position, e.g., a therapy bed used for aesthetic services, massages, and the like, in which the face is to be accommodated at a holed position, among others.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A control method for a device utilizing an electroencephalogram, comprising:

step (a) of presenting a visual stimulation concerning a manipulation menu for a device;

step (b) of measuring a plurality of event-related potentials after the visual stimulation is presented, where a plurality of event-related potentials based on a timing of presenting the visual stimulation as a starting point are measured from a potential difference between each of a plurality of electrodes worn on a face of a user and at least one reference electrode worn in an ear periphery of the user;

step (c) of, from each of the plurality of measured event-related potentials, and using an electroencephalogram characteristic extraction section, extracting electroencephalogram data which is at 5 Hz or less and contains a predetermined time section, wherein the predetermined time section is a zone from 200 ms to 400 ms based on the presenting of the visual stimulation as a starting point, and combining the extracted electroencephalogram data into electroencephalogram characteristic data;

step (d) of comparing the electroencephalogram characteristic data against reference data using a determination section, the reference data being prepared in advance for determining a desire to select an item in the manipulation menu; and step (e) of, based on a result of comparison of step (d), executing a manipulation of the device corresponding to the item in the manipulation menu.

2. The control method of claim 1, wherein step (b) measures the plurality of event-related potentials by using at least one reference electrode worn in each one of two ear peripheries of the user.

3. The control method of claim 2, further comprising:

step (f) of, based on electrical characteristics between each of the plurality of electrodes worn on the face of the user and the at least one reference electrode worn in each one of two ear peripheries of the user, determining a state of attachment of each of the plurality of electrodes and the at least one reference electrode; and step (g) of, based on a result of determination of step (f), determining a combination of electrodes for measuring the plurality of event-related potentials at step (b).

4. The control method of claim 3, wherein step (g) detects, among combinations of electrodes obtained by respectively combining a plurality of electrodes worn on the face of the user and the at least one reference electrode worn in each one of two ear peripheries of the user, a plurality of combinations of electrodes of which measured values of the plurality of event-related potentials each exceed a threshold value, and searches for an electrode which is commonly included among the plurality of combinations of electrodes to identify an electrode whose state of attachment is insufficient.

5. The control method of claim 4, wherein the electrode identified at step (g) is notified in a distinguishable manner.

6. The control method of claim 2, wherein step (b) measures the plurality of event-related potentials by using an electrode worn in at least one of a position above a right eye and a position above a left eye of the user.

7. The control method of claim 1, wherein step (b) measures the plurality of event-related potentials by using an electrode worn in at least one of a position above a right eye and a position above a left eye of the user.

8. The control method of claim 1, wherein step (c) extracts, from waveforms of the plurality of measured event-related potentials, electroencephalogram data representing characteristic features of the waveforms in terms of time and frequency.

9. The control method of claim 8, wherein step (c) subjects the measured waveforms of the electroencephalograms to a wavelet transform to extract electroencephalogram data representing characteristic features of the waveforms in terms of time and frequency.

10. The control method of claim 1, wherein step (c) extracts, from waveforms of the plurality of event-related potentials measured with the at least one reference electrode in the ear periphery and the plurality of electrodes on the face, data representing a characteristic feature of each waveform, and generates a single piece of electroencephalogram characteristic data based on the respective data.

11. The control method of claim 1, wherein step (b) of measuring a plurality of event-related potentials after the visual stimulation is presented includes measuring a potential difference between an electrode worn alongside the left eye and the at least one reference electrode worn in the right ear periphery.

12. The control method of claim 1, wherein step (b) of measuring a plurality of event-related potentials after the visual stimulation is presented includes measuring a potential difference between an electrode worn alongside the right eye and the at least one reference electrode worn in the left ear periphery.

13. An electroencephalogram interface system comprising:

an output section for visually presenting a manipulation menu;

a plurality of electrodes respectively configured to be worn in an ear periphery and on a face of a user for measuring electroencephalograms of the user;

an electroencephalogram characteristic extraction section configured to extract electroencephalogram data which is at 5 Hz or less and contains a predetermined time section from each of a plurality of event-related potentials measured from potential differences between a plurality of electrodes configured to be worn on the face and at least one reference electrode configured to be worn in the ear periphery based on a timing of presenting the manipulation menu as a starting point, wherein the predetermined time section is a zone from 200 ms to 400 ms based on the presenting of the manipulation menu as a starting point, and combining the extracted electroencephalogram data into electroencephalogram characteristic data representing characteristic features of waveforms of the plurality of measured event-related potentials; and a determination section configured to determine a similarity level by comparing the electroencephalogram characteristic data against reference data which is prepared in advance for determining a desire to select an item in the manipulation menu, and controlling a device based on a result of determination.

14. The electroencephalogram interface system of claim 13, wherein, the output section is a display; and the determination section controls a displayed substance on the display based on the result of determination.

15. The electroencephalogram interface system of claim 14, further comprising a transmission section for outputting a control signal for an external device, wherein the determination section outputs the control signal based on the result of determination, and controls an operation of the external device based on the control signal.

16. A control device for a display device, the control device and the display device together constituting an electroencephalogram interface system, the control device comprising:

a communication section for communicating with the display device to cause the display device to visually present a manipulation menu;

a plurality of electrodes respectively configured to be worn in an ear periphery and on a face of a user for measuring electroencephalograms of the user;

an electroencephalogram characteristic extraction section configured to extract electroencephalogram data which is at 5 Hz or less and contains a predetermined time section from each of a plurality of event-related potentials measured from potential differences between a plurality of electrodes configured to be worn on the face and at least one reference electrode configured to be worn in the ear periphery based on a timing of presenting the manipulation menu as a starting point, wherein the predetermined time section is a zone from 200 ms to 400 ms based on the presenting of the manipulation menu as a starting point, and combining the extracted electroencephalogram data into electroencephalogram characteristic data representing characteristic features of waveforms of the plurality of measured event-related potentials; and a determination section configured to determine a similarity level by comparing the electroencephalogram characteristic data against reference data which is prepared in advance for determining a desire to select an item in the manipulation menu, and controlling a device based on a result of determination.

* * * * *